US006846817B2

(12) United States Patent
Efange

(10) Patent No.: US 6,846,817 B2
(45) Date of Patent: Jan. 25, 2005

(54) NICOTINE RECEPTOR LIGANDS

(75) Inventor: S. Mbua Ngale Efange, Plymouth, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/997,718

(22) Filed: Nov. 30, 2001

(65) Prior Publication Data
US 2003/0027810 A1 Feb. 6, 2003

Related U.S. Application Data

(63) Continuation of application No. PCT/US00/15348, filed on Jun. 2, 2000.
(60) Provisional application No. 60/137,099, filed on Jun. 2, 1999.

(51) Int. Cl.$^7$ ................ C07D 405/04; A61K 31/153; A61K 31/4025; A61P 25/34
(52) U.S. Cl. ............... 514/228.2; 514/210.19; 514/233.5; 514/256; 514/307; 514/320; 514/337; 514/422; 544/62; 544/151; 544/153; 544/333; 548/525; 548/950; 546/139; 546/144; 546/148; 546/196; 546/282.7; 546/284.1
(58) Field of Search .............. 514/210.19, 228.2, 514/233.5, 307, 320, 337, 442; 544/62, 151, 153, 333; 546/144, 139, 148, 196, 282.7, 284.1; 548/525, 950

(56) References Cited

U.S. PATENT DOCUMENTS

| | | | | |
|---|---|---|---|---|
| 3,927,023 A | * | 12/1975 | Brown et al. ............ 548/311.4 |
| 4,173,640 A | | 11/1979 | Hauck et al. ............. 424/267 |
| 4,210,655 A | | 7/1980 | Schenker et al. .......... 514/320 |
| 4,339,384 A | * | 7/1982 | Maillard et al. .......... 548/525 |
| 4,411,908 A | * | 10/1983 | Chapleo et al. ........... 514/385 |
| 4,775,675 A | | 10/1988 | Gyorgydeak et al. ....... 514/307 |
| 4,940,710 A | * | 7/1990 | Sum et al. ............. 514/253.08 |
| 5,847,159 A | | 12/1998 | Kai et al. ................ 548/578 |

FOREIGN PATENT DOCUMENTS

| | | | |
|---|---|---|---|
| CH | 613452 | 9/1979 | ......... C07D/405/04 |
| DE | 2408476 A | * 9/1974 | |
| DE | 2408476 | 12/1975 | ........... C07D/29/38 |

(List continued on next page.)

OTHER PUBLICATIONS

Schmitt, J.D. et al, "Annual Reports Med. Chem.", 35, 2000, 41–51.*

Shridhar, D. R.; Sastry, C. V. Reddy; Lal, Kulbhushan; Rao, C. Seshagiri; Taneja, V., Indian Journal of Chemistry, Section B: Organic Chemistry Including Medicinal Chemistry, 18B(3), 254–6 (English) 1979.*

(List continued on next page.)

Primary Examiner—Mark L. Berch
(74) Attorney, Agent, or Firm—Schwegman, Lundberg, Woessner & Kluth, P.A.

(57) ABSTRACT

The invention provides nicotine receptor agonists of formula I:

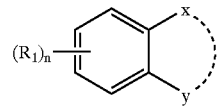

wherein $R_1$, x, y, and n have any of the values given in the specification, or a pharmaceutically acceptable salt thereof, as well as pharmaceutical compositions comprising such a compound or salt, methods for preparing such a compound or salt, and methods for modulating (e.g. antagonizing or activating) nicotine receptors with such a compound or salt.

30 Claims, 13 Drawing Sheets

FOREIGN PATENT DOCUMENTS

| | | | | |
|---|---|---|---|---|
| EP | 115142 A1 | * | 8/1984 | |
| JP | 59/204190 A2 | * | 11/1984 | |
| JP | 10-175862 | | 6/1998 | ........ A61K/31/40 |
| WO | WO 97/23216 A1 | * | 7/1997 | |
| WO | 97/23216 | | 7/1997 | ........ A61K/31/445 |
| WO | 97/45424 | | 12/1997 | ........ C07D/403/06 |
| WO | WO 00/76990 A1 | * | 12/2000 | |

OTHER PUBLICATIONS

Johansson, Gary; Brisander, Magnus; Sundquist, Staffan; Hacksell, Uli, Chirality, 10(9), 813–820 (English) 1998.*

Document No. 102:185092 Benzofuranylmorpholines. (Kaken Pharmaceutical Co., Ltd., Japan). Jpn. Kokai Tokkyo Koho JP 59204190 A2, Chemical Abstracts.*

Chapleo, C.B., et al., "a–Adrenoreceptor reagents. 2. Effects of modification of the 1,4–benzodioxan ring system on a–adrenoreceptor activity", *Journal of Medicinal Chemistry*, 27 (5), pp. 570–576, (1984).

Dolby, L.J., et al., "New reactions of 3–vinylindoles", *Tet, vol. 24, No. 21*, 6377–6386, (1968).

* cited by examiner

ABT-418

ABT-594

ABT-089

RJR-2403

SIB-1765F

GTS-21

NICOTINE RECEPTOR LIGANDS

RELATED APPLICATIONS

This application is a continuation under 35 U.S.C. 111(a) of International Application No. PCT/US00/15348 filed Jun. 2, 2000, and published as WO 00/73269 A2 on Dec. 7, 2000, which claimed priority from provisional U.S. patent application Ser. No. 60/137,099, filed Jun. 2, 1999, both of which applications are incorporated herein by reference.

GOVERNMENT FUNDING

The invention described herein was made with government support under Grant Number NS33742 and AG 13621 awarded by the National Institutes of Health. The United States Government has certain rights in the invention.

BACKGROUND OF THE INVENTION

Acetylcholine, a major neurotransmitter in mammalian organisms, is released from central, sympathetic and peripheral neurons. Acetylcholine is involved in a wide range of biological functions including motor, sensory, learning and memory, sexual activity, sleep, and autonomic control of cardiovascular, respiratory, gastrointestinal and urogenital functions. Modulation of cholinergic function has been found to have beneficial effects in a number of pathologies such as Alzheimer's disease, Parkinson's disease and olivopontocerebellar atrophy.

Actions of the neurotransmitter acetylcholine are modulated by two classes of receptors, muscarinic and nicotinic, on the basis of the effects of the prototypical cholinergic agonists, muscarine and nicotine. Nicotine administration increases dopamine efflux in the striatum, nucleus accumbens and cortex. Nicotine administration also causes norepinephrine release in cortex and hippocampus and glutamate release in the cortex. The effects of nicotine on glutamate have also been demonstrated in behavioral tests where NMDA antagonist MK-801 eliminated the memory improvement caused by nicotine. Nicotine also stimulates acetylcholine release and thus exerts some of its actions via muscarinic receptors.

Nicotine affects cardiovascular function by sympathetic neural stimulation. The endocrine-mediating effects of nicotine release include a release of beta-endorphins, and stimulation of ACTH and cortisol release. Nicotine also induces lipolysis and subsequent release of free fatty acids into the circulation.

Behavioral experimentation in rodents, monkeys and humans has shown that nicotine agonists can improve performance in cognitive tasks while nicotine antagonists impair performance of those tasks. The cognition-enhancing effects of nicotine have beneficial effects on attention deficit patients.

Epidemiological studies suggest that smokers have approximately a two-fold lower risk of being diagnosed with Parkinson's disease than non-smokers and nicotine may be partly responsible for this apparent protective affect. A similar disparity is observed between smokers and non-smokers for neuroleptic induced Parkinsonism.

Mammalian nicotine receptors belong to a class of pentameric ligand gated ion channels. In a rat brain, at least eight $\alpha(\alpha_2-\alpha_9)$ and three 62 ($\beta_2-\beta_4$) subunits have been cloned. In the mammalian brain, the most abundant subtype is $\alpha_4\beta_2$.

In recent years, a realization that nicotinic acetylcholine receptor mediated biochemical activities can exert beneficial effects on human neurological disorders has fueled interest in the development of compounds that have better safety and pharmacokinetic profiles than nicotine. These efforts have resulted in the development of the compounds ABT418, ABT089, ABT-594, GTS-21 and SIB-1765f and RJR-2403, which are illustrated in FIG. 1.

Anabaseine and its derivative GTS-21 are known to interact with both $\alpha_4\beta_2$ and $\alpha_7$ nicotinic acetylcholine receptor subtypes. In functional assays, GTS-21 appears to act as a potent partial agonist in $\alpha_7$ receptors. On the other hand, it is a weak partial agonist at $\alpha_4\beta_2$ receptors.

The nicotine analog SIB-1765f displays comparable binding affinity with nicotine in rat cortical membranes. Electrophysiological recordings of current responses in *Xenopus* oocytes expressing recombinant human nicotinic acetylcholine receptors revealed that SIB-1508y produced currents that ranged between 20 and 50% of the response elicited by an equimolar concentration of acetylcholine in oocytes expressing the $\alpha_2\beta_2$, $\alpha_2\beta_4$, $\alpha_3\beta_2$, $\alpha_4\beta_2$ and $\alpha_4\beta_4$ nicotinic acetylcholine receptor subtypes. No detectable response was obtained from cells expressing the $\alpha_7$ human subtype and only a minimal response was obtained from cells expressing the $\alpha_3\beta_4$ subtype. In contrast, nicotine is a potent agonist for both $\alpha_7$ and $\alpha_3\beta_4$ nicotinic acetylcholine receptor subtypes.

RJR-2403 displaces [$^3$H]-nicotine binding in rat cortex with moderately high potency (Ki=26±3 nM) reflecting high affinity for the $\alpha_4\beta_2$ nicotinic acetylcholine receptor subtype. In contrast, the compound is significantly less potent at the $\alpha_7$ subtype (Ki=36 micromolar). RJR-2403 is also comparable to nicotine in evoking $^{86}$Rb$^+$ efflux from rat thalamic synaptosomes, but only one tenth as active as nicotine in stimulating [$^3$H]-dopamine release from striatal synaptosomes. At concentrations of up to 1 mM, RJR-2403 does not significantly activate nicotinic acetylcholine receptor as PC12 cells or human muscle nicotinic acetylcholine receptor subtype. The low potency of RJR-2403 at these peripheral nicotinic acetylcholine receptors led investigators to conclude that in contrast to nicotine this compound is selective for CNS nicotinic acetylcholine receptors.

ABT-418 is a potent nicotine ligand which interacts stereoselectively with a neuronal [$^3$H]-cytisine binding site (Ki=4.5 nanomolar). ABT-418 also activates human a nicotinic acetylcholine receptors expressed in *Xenopus* oocytes and stimulates dopamine release from striatal slices. However, the potency of this compound is lower than that of (−)-nicotine. Because the $\alpha_3$ subunit has been linked to dopamine release, the lower potency of ABT418 in the latter assay is viewed as an indication that this compound displays lower affinity for the $\alpha_3$ subunit than (−)-nicotine.

ABT-089 and ABT-594 are members of the 3-pyridyl alkyl ether class of nicotinic acetylcholine receptor ligands. Structurally, both compounds differ from nicotine and ABT-418 in that the pyridyl and cycloalkylamine fragments are separated by an oxymethylene bridge. The presence of this bridge results in increased flexibility relative to nicotine and increased separation between the centroid of the pyridyl moiety and the amino group of the cycloalkylamine.

ABT-594 is a potent inhibitor of [$^3$H]-nicotine binding to the neuronal $\alpha_4\beta_2$ nicotinic acetylcholine receptor subtype in rat brain (Ki=37 picomolar) and in cells expressing the human receptor (Ki=55 picomolar). Compared to ABT-594, ABT-089 is about 300-fold less potent as an inhibitor of [$^3$H]-nicotine binding to the $\alpha_4\beta_2$ nicotinic-acetylcholine subtype. However, the affinity of this analog for the $\alpha_7$ neuronal subtype and ganglionic nicotinic acetylcholine receptors is comparable to that of ABT-594.

Currently, there is a need for novel and effective treatments for disorders such as Alzheimer's disease, Parkinson's disease, schizophrenia, depression, attention deficit/hyperactivity disorder, neuropathic pain, ulcerative colitis, urinary incontinence, and olivopontocerebellar atrophy. While nicotine has been shown to exhibit beneficial effects in treating such disorders, its' use has been associated with detrimental side effects on cardiovascular and gastrointestinal function. Consequently, there is a need for novel nicotinic agonists or antagonists that can effectively treat these disorders without eliciting the detrimental side effects of nicotine. There is also a need for pharmacological tools for the further study of the physiological processes associated with disfunctional acetylcholine production.

SUMMARY OF THE INVENTION

The present invention relates to agents and methods that are useful for modulating nicotinic receptor function and that have use in modulation of neuroendocrine function, respiration, mood, motor control and function, memory and cognition. In particular, the invention provides compounds that act as nicotine agonists.

Accordingly there is provided a compound of the invention which is a compound of formula I:

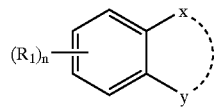

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy, thio, $C(R_c)(R_d)$, or $NR_f$;

y is an optionally unsaturated $C_2-C_4$ alkene chain substituted on the carbon adjacent x with $-(CH_2)_mR_e$, and optionally substituted on a carbon other than the carbon bearing $-(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ together with the nitrogen to which they are attached are a 5–6 membered heterocyclic ring (e.g. a pyrrolidino, piperidino or morpholino ring);

$R_c$ and $R_d$ are each independently absent, hydrogen, or $(C_1-C_6)$alkyl;

$R_e$ is a saturated or partially unsaturated 4, 5, 6, or 7 membered heterocyclic ring comprising two or more carbon atoms, a nitrogen atom, and optionally comprising an additional heteroatom selected from oxy, thio, or nitrogen, or a bicyclic benz-derivative or a bicyclic ring derived by fusing a propylene, trimethylene, or tetramethylene diradical to such a heterocycle, wherein any nitrogen atom of $R_e$ is substituted with hydrogen, $(C_1-C_6)$alkyl, or $(C_1-C_6)$alkanoyl and wherein any ring carbon of $R_e$ is optionally substituted with one or more (e.g. 1, 2, 3, or 4) $R_k$;

$R_f$ is hydrogen, $(C_1-C_6)$alkyl, $(C_1-C_6)$alkanoyl, aryl, or aryl$(C_1-C_6)$alkyl;

each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_2-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or $C(=O)NR_aR_b$;

wherein each aryl or heteroaryl is optionally substituted with one or more (e.g. 1, 2, 3, or 4) substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$.

or a pharmaceutically acceptable salt thereof;

provided $R_1$ is not 6-hydroxy; when x is oxy; y is $-(CH_2)_3-$; n is 1; and $R_e$ is 2-piperidinyl.

The invention also provides a pharmaceutical composition comprising a compound of formula I or a pharmaceutically acceptable salt thereof, in combination with a pharmaceutically acceptable diluent or carrier.

The invention also provides a therapeutic method for preventing or treating a pathological condition or symptom in a mammal, such as a human, wherein the activity of a nicotine receptor is implicated and activiation (i.e., agonism) of its action is desired, comprising administering to a mammal in need of such therapy, an effective amount of a compound of formula I or pharmaceutically acceptable salts thereof.

The invention also provides for the use of a compound of formula I in medical therapy (e.g. for treating Alzheimer's disease, Parkinson's disease, schizophrenia, depression, attention deficit/hyperactivity disorder, neuropathic pain, ulcerative colitis, urinary incontinence, and olivopontocerebellar atrophy), as well as the use of a compound of formula I for the manufacture of a medicament for the treatment of a pathological condition or symptom in a mammal (e.g. a human) wherein agonism of a nicotine receptor is desired (e.g. Alzheimer's disease, Parkinson's disease, schizophrenia, depression, attention deficit/hyperactivity disorder, neuropathic pain, ulcerative colitis, urinary incontinence, and olivopontocerebellar atrophy).

The invention also provides synthetic methods and intermediates useful for preparing compounds of formulas I or salts thereof.

The invention also provides compounds of formula I labeled with one or more radionuclides. Such radiolabeled compounds are useful as pharmacologic tools to investigate nicotinic-acetylcholine receptor activity and function.

The invention also provides a method for binding a compound of formula I (e.g. a radiolabeled compound of formula I) to nicotine receptors comprising contacting tissue comprising the receptors, in vivo or in vitro, with an amount of a compound of formula I effective to bind to said receptors. Tissue comprising ligand bound nicotine receptors can be used to measure the selectivity of test compounds for specific receptor subtypes, or can be used as a tool to identify potential therapeutic agents for the treatment of diseases or conditions associated with disfunctional acetylcholine production, by contacting the agents with the ligand-receptor complexes, and measuring the extent of displacement of the ligand and/or binding of the agent.

DETAILED DESCRIPTION

Figure 1:
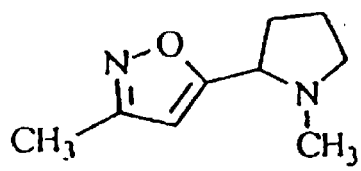
FIG. 1 shows the compounds ABT-418, ABT-089, ABT-594, GTS-21, SIB-1765R and RJR-2403.
Figure 1:
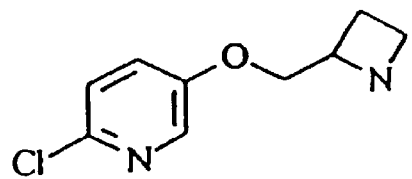
Figure 1:
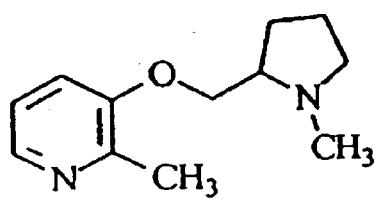
Figure 1:
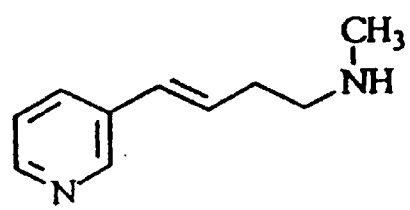
Figure 1:
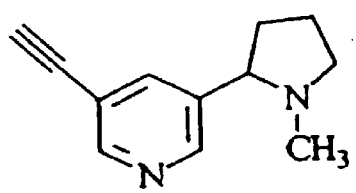
Figure 1:
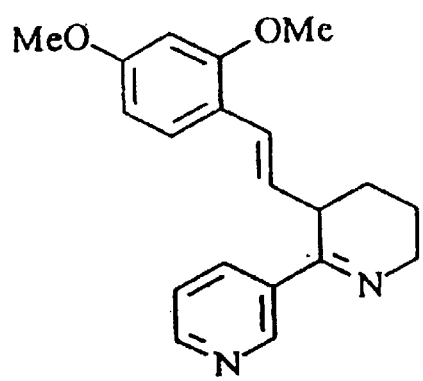

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine nicotine agonist (or antagonist) activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for x is oxy, sulfur, or N(X).

A specific value for $R_e$ is azetidinyl, pyrrolidinyl, piperidinyl, morpholinyl, 1,2,3,4-tetrahydroisoquinolyl, 3,4,5,6-tetrahydropyridyl, or thiomorpholinyl, wherein the ring $R_e$ is substituted on nitrogen with hydrogen, $(C_1-C_6)$alkyl, or $(C_1-C_6)$alkanoyl.

A specific value for $R_e$ is azetidinyl, pyrrolidinyl, piperidinyl, morpholinyl, or thiomorpholinyl, wherein the ring $R_e$ is substituted on nitrogen with hydrogen, $(C_1-C_6)$alkyl, or $(C_1-C_6)$alkanoyl.

A specific value for $R_e$ is 2-azetidinyl, 1-methyl-2-azetidinyl, 1-methyl-2-pyrrolidinyl, 1-methyl-2-piperidinyl, N-methyl-3-morpholinyl, or N-methyl-3-thiomorpholinyl.

A specific compound of formula I is a compound of the following formula:

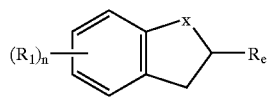

or a pharmaceutically acceptable salt thereof; wherein $R_1$, x, $R_e$ and n have any of the values or specific values described herein for the corresponding radical in a compound of formula I.

A specific compound of formula I is a compound of the following formula:

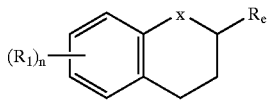

or a pharmaceutically acceptable salt thereof; wherein $R_1$, x, $R_e$, and n have any of the values or specific values described herein for the corresponding radical in a compound of formula I.

A specific compound of formula I is a compound of the following formula:

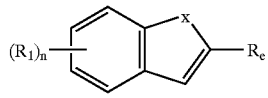

or a pharmaceutically acceptable salt thereof; wherein $R_1$, x, $R_e$, and n have any of the values or specific values described herein for the corresponding radical in a compound of formula I.

A specific compound of formula I is a compound of the following formula:

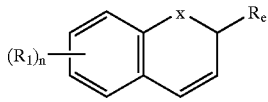

or a pharmaceutically acceptable salt thereof; wherein $R_1$, x, $R_e$, and n have any of the values or specific values described herein for the corresponding radical in a compound of formula I.

A specific compound of formula I is a compound of the following formula:

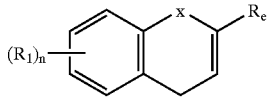

or a pharmaceutically acceptable salt thereof; wherein $R_1$, x, $R_e$, and n have any of the values or specific values described herein for the corresponding radical in a compound of formula I.

A specific compound of formula I is a compound of the following formula:

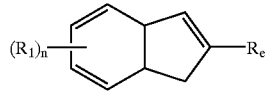

or a pharmaceutically acceptable salt thereof; wherein $R_1$, $R_e$, and n have any of the values or specific values described herein for the corresponding radical in a compound of formula I.

A specific compound of formula I is a compound of the following formula:

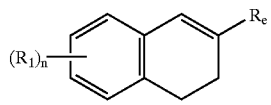

or a pharmaceutically acceptable salt thereof; wherein $R_1$, $R_e$, and n have any of the values or specific values described herein for the corresponding radical in a compound of formula I.

A specific compound of formula I is a compound of a compound of formula I:

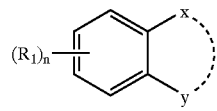

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy, thio, $C(R_c)(R_d)$, or $NR_f$;

y is an optionally unsaturated $C_2-C_4$ alkene chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_1)$alkyl, $(C_1-C_6)$alkanoyl, aryl, or aryl$(C_1-C_6)$alkyl; or $R_a$ and $R_b$ together with the nitrogen to which they are attached are a 5–6 membered heterocyclic ring (e.g. a pyrrolidino, piperidino or morpholino ring);

$R_c$ and $R_d$ are each independently absent, hydrogen, or $(C_1-C_6)$alkyl;

$R_e$ is a saturated or partially unsaturated 4, 5, 6, or 7 membered heterocyclic ring comprising two or more carbon atoms, a nitrogen atom, and optionally comprising an additional heteroatom selected from oxy, thio, or nitrogen, wherein any nitrogen atom is substituted with hydrogen, $(C_1-C_6)$alkyl, or $(C_1-C_6)$alkanoyl; and $R_f$ is hydrogen, $(C_1-C_6)$alkyl, $(C_1-C_6)$alkanoyl, aryl, or aryl$(C_1-C_6)$alkyl;

or a pharmaceutically acceptable salt thereof;

provided $R_1$ is is not 6-hydroxy; when x is oxy; y is —$(CH_2)_3$—; n is 1; and is 2-piperidinyl.

A preferred compound of the invention is erythro-7-Hydroxy-2-(1-methylpyrrolidin-2-yl)chroman (11); or a pharmaceutically acceptable salt thereof.

A preferred compound of the invention is threo-7-Hydroxy-2-(1-methylpyrrolidin-2-yl)chroman (12); or a pharmaceutically acceptable salt thereof.

Another preferred compound of the invention is erythro-7-Hydroxy-2-(1-methylpiperidin-2-yl)chroman (3); or a pharmaceutically acceptable salt thereof.

Another preferred compound of the invention is threo-7-Hydroxy-2-(1-methylpiperidin-2-yl)chroman (8); or a pharmaceutically acceptable salt thereof.

A specific compound of the invention is a compound of formula I as described herein wherein $R_e$ is of the formula:

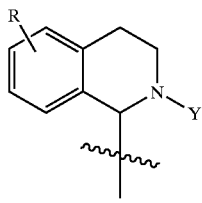

wherein Y is hydrogen or methyl; and R is hydrogen, hydroxy, halogen, $(C_1-C_3)$alkyl, $(C_1-C_3)$alkoxy, $(C_1-C_3)$ alkanoyl, cyano, nitro, or amino; or a pharmaceutically acceptable salt thereof.

A specific compound of the invention is a compound of formula I as described herein wherein $R_e$ is of the formula:

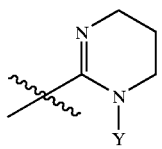

wherein Y is hydrogen or methyl; or a pharmaceutically acceptable salt thereof.

A specific compound of the invention is a compound of formula I as described herein wherein $R_e$ is of the formula:

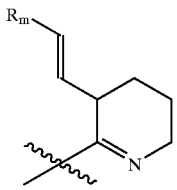

wherein $R_m$ is phenyl or heteroaryl, wherein said phenyl or heteroaryl is optionally substituted with one or more substituents independently selected from halo, hydroxy, nitro, cyano, trifluoromethyl, trifluoromethoxy, amino, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, or $(C_3-C_6)$ cycloalkyl; or a pharmaceutically acceptable salt thereof.

Synthetic methods for preparing compounds of formula I are illustrated by the following procedures in which the meanings of the generic radicals are as given above unless otherwise qualified.

Figure 2:
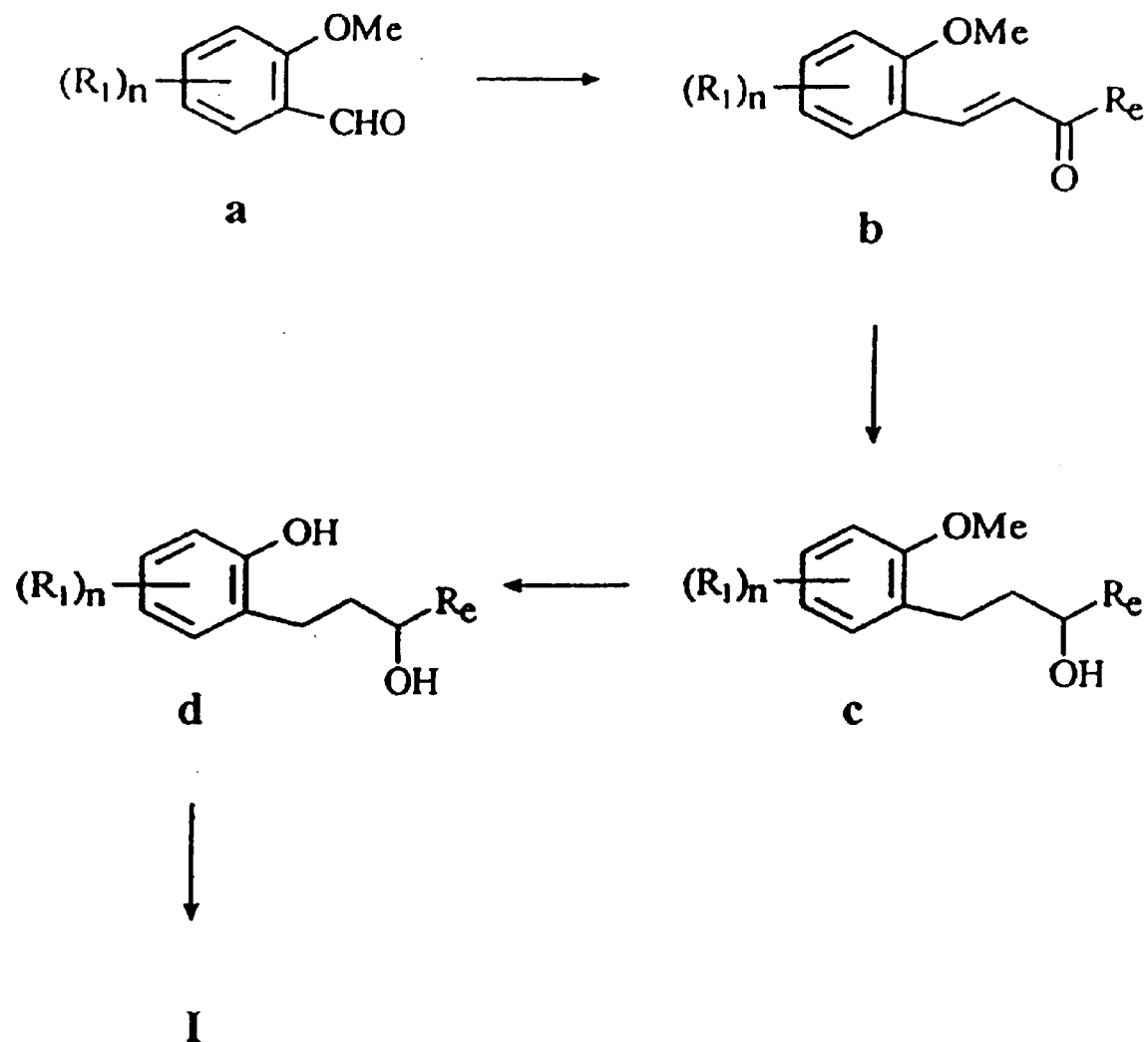
FIG. 2 illustrates the preparation of compounds of formula I.

Generally, a compound of formula I can be prepared as illustrated in FIG. 2. Reaction of a substituted anisaldehyde of formula a with a compound of formula $CH_2=CHC(=O)$ $R_e$ provides a compound of formula b. Stepwise reduction of the unsaturated ketone gives a saturated alcohol c which can be demethylated (e.g. with $BBr_3$) to give phenol d. Intramolecular cyclization (e.g. via the Mitsunobu reaction), gives a compound of formula I, as a mixture of threo to erythro isomers.

Figure 3:
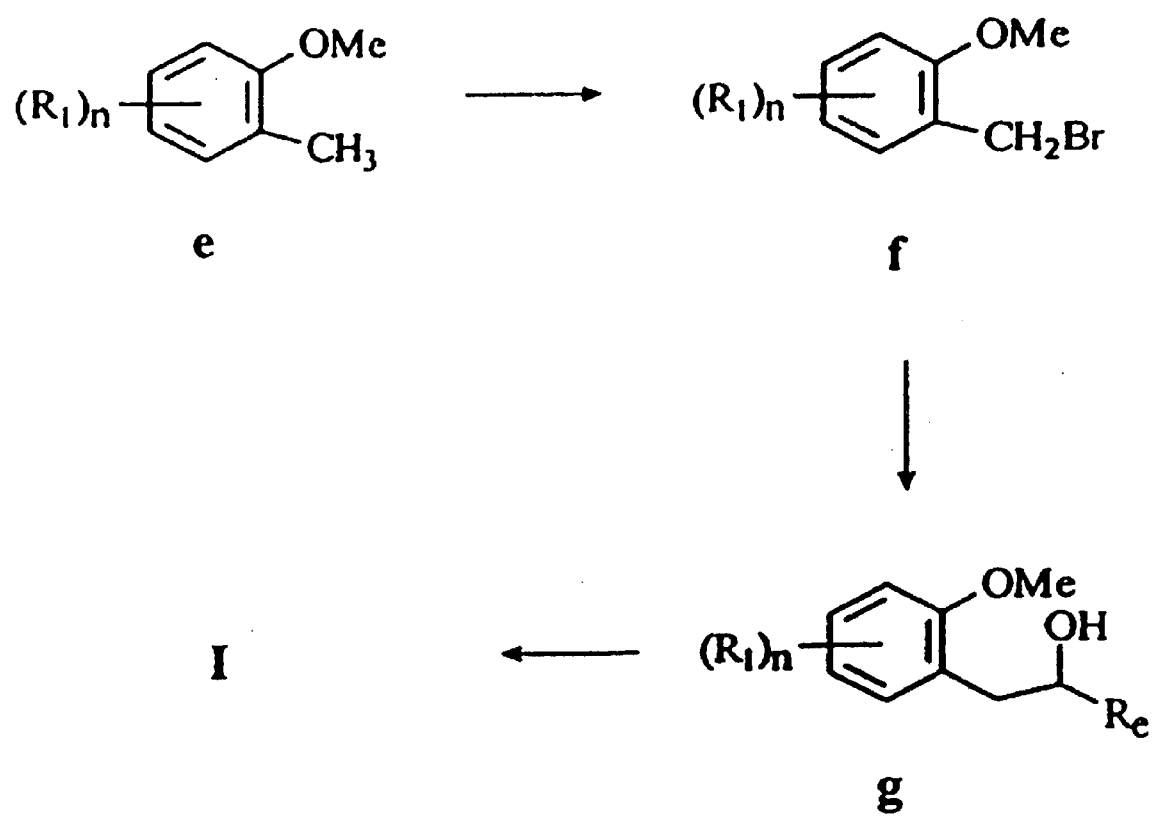
FIG. 3 illustrates the preparation of compounds of formula I.

Compounds of formula I can also be prepared as illustrated in FIG. 3. Bromination of toluene e (e.g. with NBS, $CCl_4$, and benzoyl peroxide as catalysts) yields a compound of formula f. Grignard formation followed by reaction with the requisite aldehyde gives an alcohol of formula g, which can be demethylated (e.g. with $BBr_3$ and $CH_2Cl_2$) and cyclized (e.g. with DEAD, triphenylphosphine and THF to give a compound of formula I.

Figure 8:
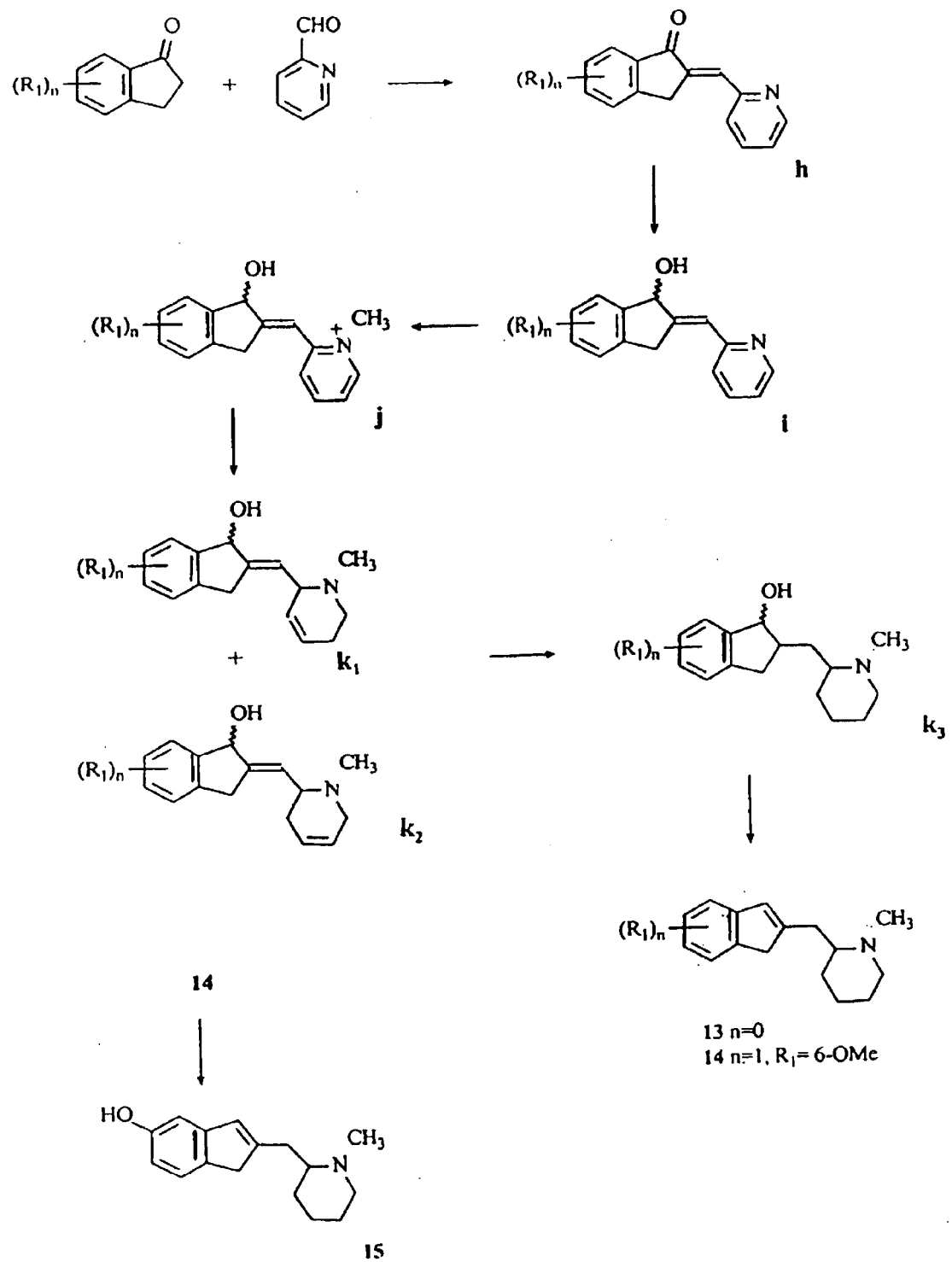
FIG. 8 illustrates the preparation of compounds of formula I.

Compounds of formula I can also be prepared as illustrated in FIG. 8, and as described in Examples 11 and 12. Condensation of 1-indanone and pyridine-2-carboxaldehyde gives a compound of formula h which can be reduced to an alcohol of formula i and allylated to give a salt of formula j. Reduction of the salt yields a mixture of isomers $k_1$ and $k_2$, which can be further reduced to give an alcohol of formula $k_3$. Dehydration provides compounds 13 and 14.

Compounds of formula I wherein $R_1$ is hydroxy can be prepared from a corresponding compound of formula I wherein $R_1$ is methoxy using a procedure similar to that described in Example 13, as illustrated in FIG. 8, for the conversion of compound 14 to compound 15.

Compounds of formula I wherein $R_e$ is piperidinyl, can be prepared from a corresponding compound of formula I wherein $R_e$ is pyridyl by reduction using procedures that are known in the art, for example, by hydrogenation in the presence of a suitable metal catalyst. Thus, compounds of formula I wherein $R_e$ is pyridyl are useful intermediates for preparing corresponding compounds of formula, I wherein $R_e$ is piperidinyl.

Figure 4:
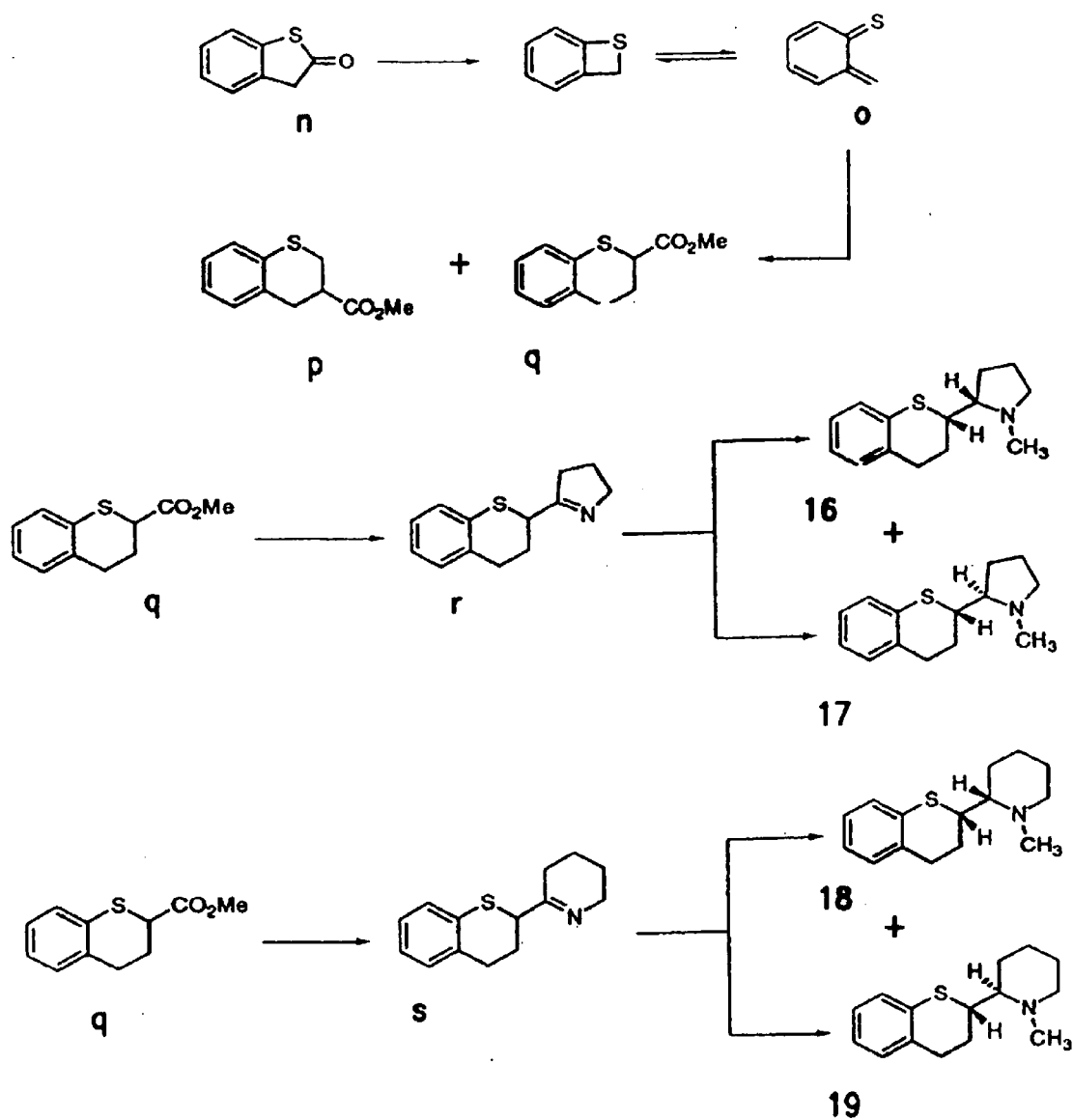
FIG. 4 illustrates the preparation of compounds of formula I.

Compounds of formula I wherein X is thio and $R_e$ is pyrrolidinyl can be prepared as illustrated in FIG. 4. Exomethylene compound o is formed via flash pyrolysis of thioester n. Diels Alder reaction of n with methyl acrylate gives thiopyran q. Condensation of q with 1-vinylpyrrolidinone, followed by acid treatment, gives a compound of formula r. Reduction of the imine moiety in compound r, followed by N-methylation, gives pyrrolidinyl derivatives 16 and 17.

Compounds of formula I wherein X is thio $R_e$ is piperidinyl are also formed from thipyran q, as also depicted in FIG. 4. Condensation of q with 1-vinylpiperidinone, followed by acid treatment, gives a compound of formula s. Reduction of the imine moiety in compound r, followed by N-methylation, gives pyrrolidinyl derivatives 18 and 19.

Figure 5:
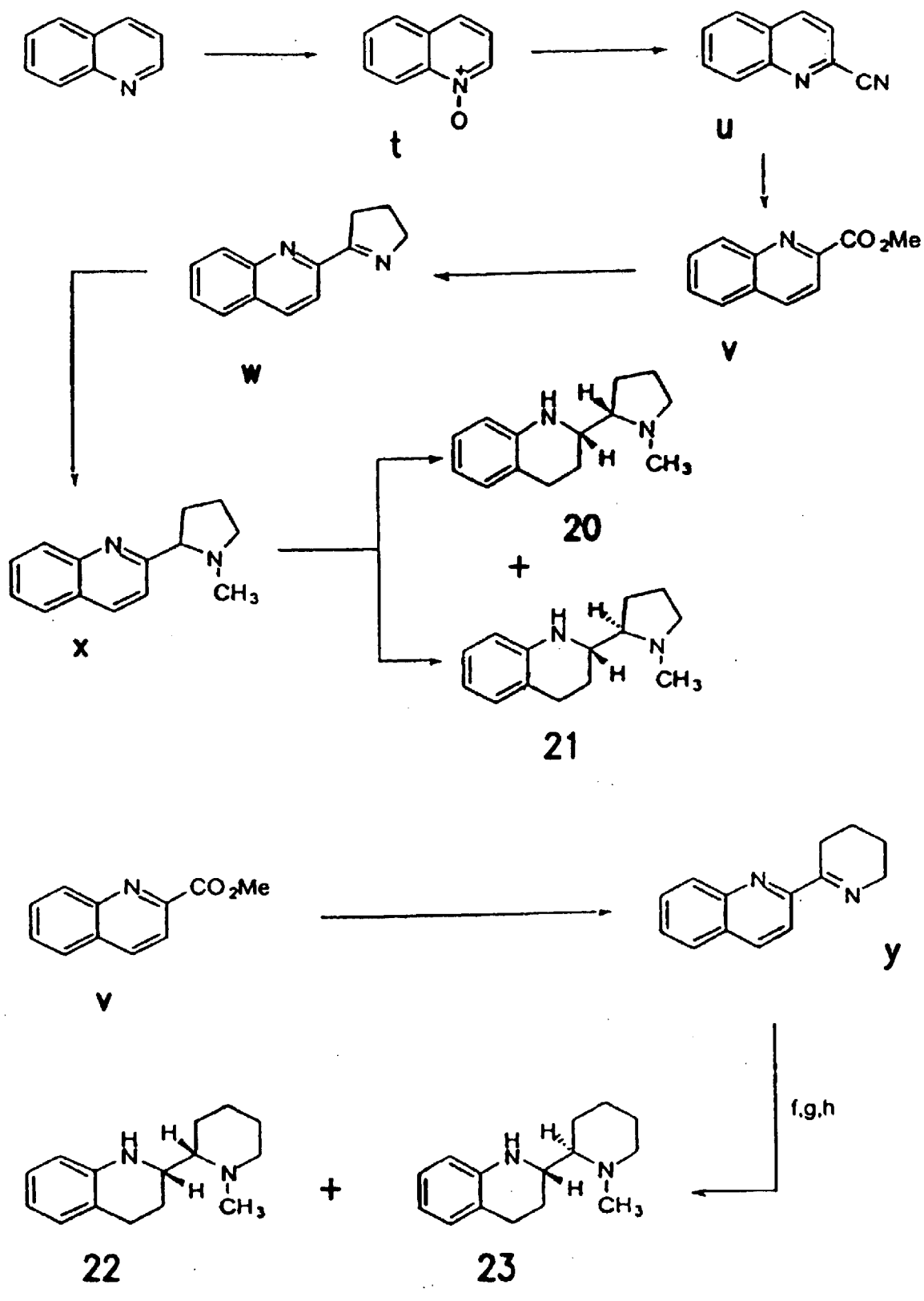
FIG. 5 illustrates the preparation of compounds of formula I.
Figure 6:
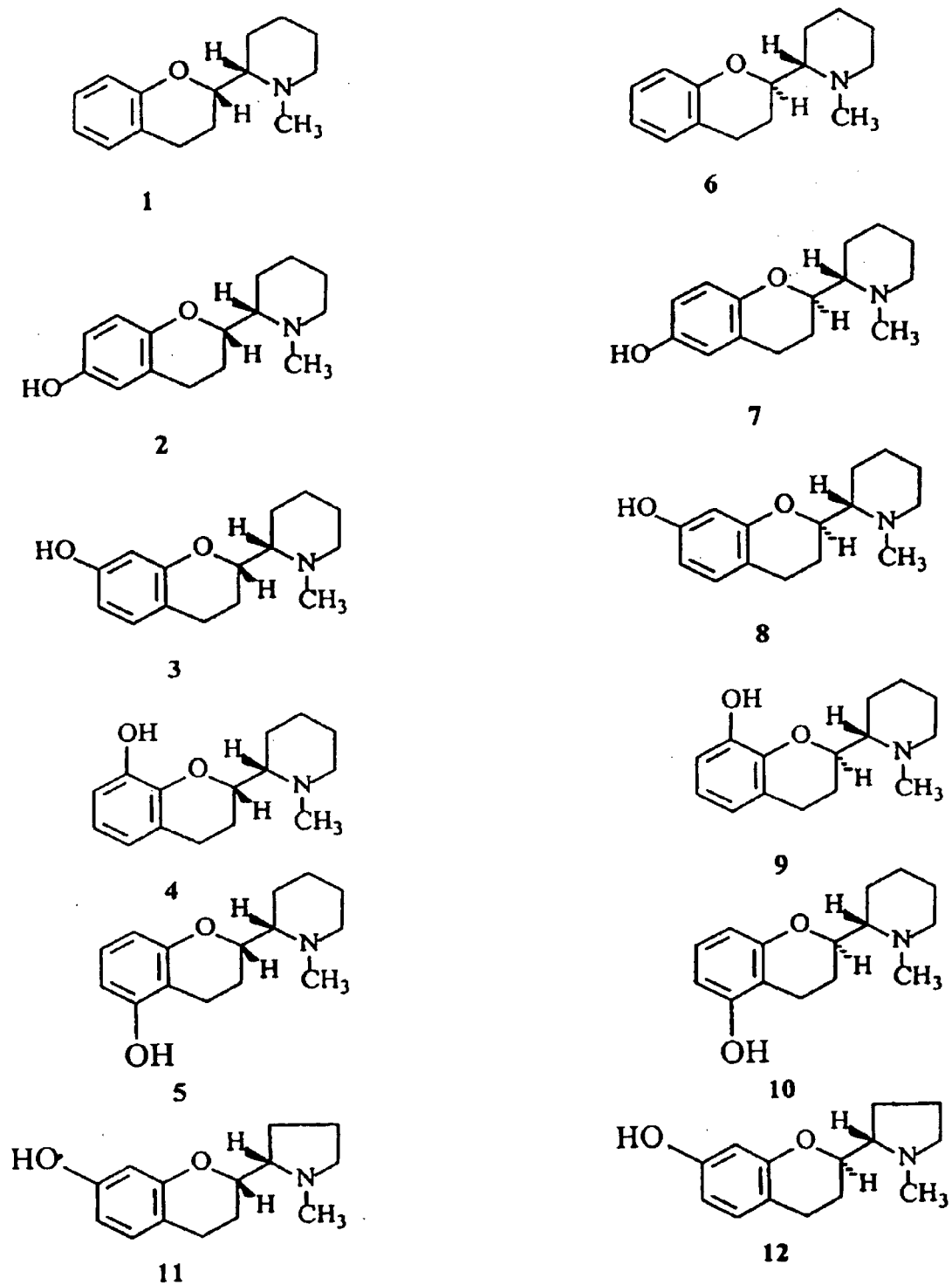
FIG. 6 illustrates representative compounds of formula I.
Figure 7:
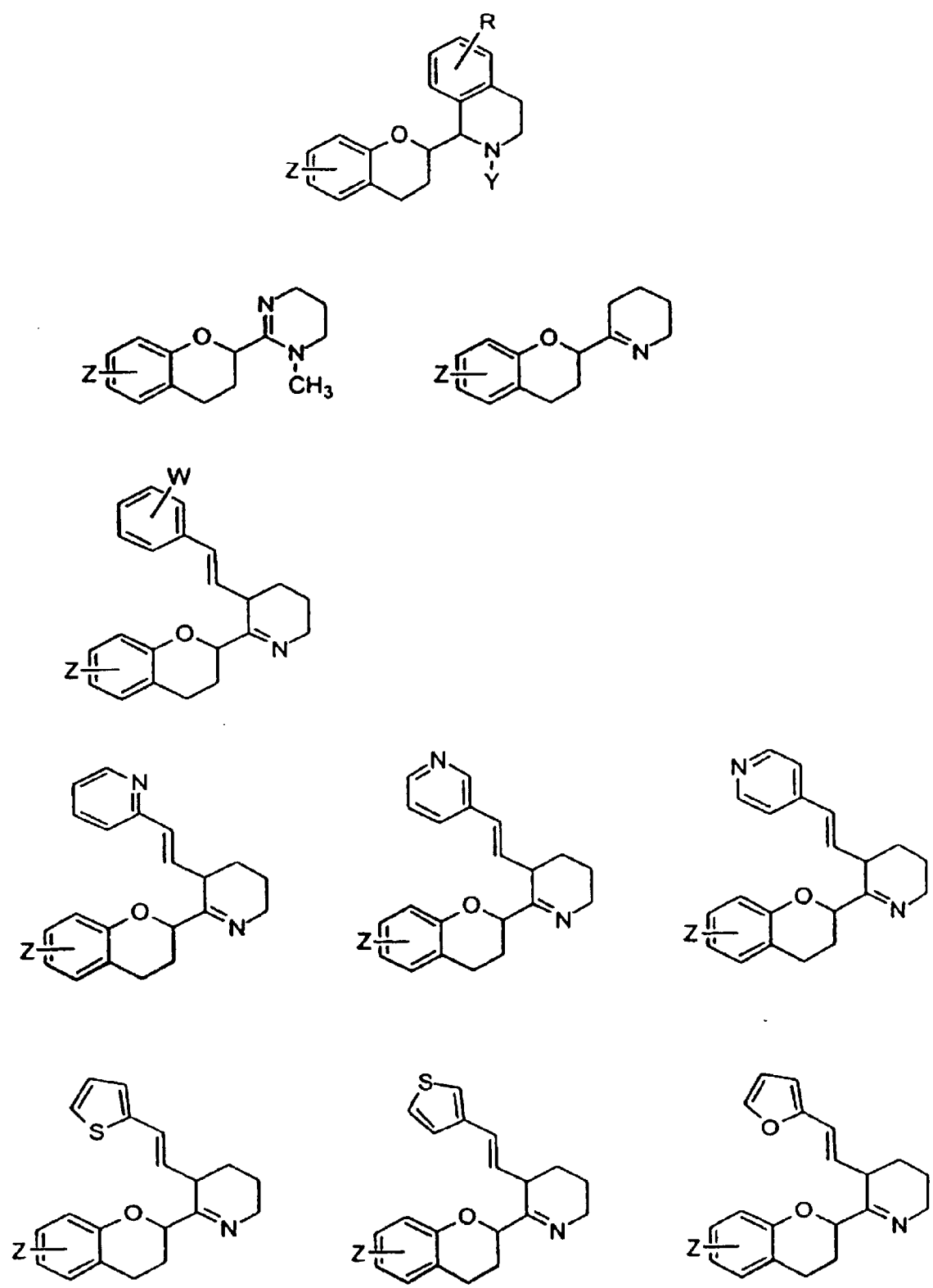
FIG. 7 illustrates representative compounds of formula I wherein Y is hydrogen or methyl; Z is hydrogen, halogen, $(C_1-C_3)$alkyl, $(C_1-C_3)$alkoxy, $(C_1-C_3)$alkanoyl, cyano, nitro, or amino; R is hydrogen, hydroxy, halogen, $(C_1-C_3)$alkyl, $(C_1-C_3)$alkoxy, $(C_1-C_3)$alkanoyl, cyano, nitro, or amino; and W is amino, cyano, nitro, halogen, or $(C_1-C_3)$alkoxy.

Compounds of formula I wherein X is $NR_f$ can be prepared as illustrated in FIG. 5. Oxidation of quinoline gives N-oxide t. Treatment of compound t with trimethylsilyl cyanide gives nitrile derivative u. Nitrile derivative u is converted to the methyl ester v via acid catalyzed hydration to provide the carboxylic acid, followed by esterification in the presence of methanol. Compounds of formula I containing pyrrolidinyl subunits can be formed from v in a stepwise fashion. Treatment of v with 1-vinyl-2-pyrrolidinone, followed by acid treatment, gives a compound of formula w. Reduction and N-methylation of w gives a compound of formula x. Compound x can be reduced to give pyrrolidinyl derivatives 20 and 21.

Compounds of formula I wherein $R_e$ is piperidinyl can also be formed from methyl ester v, as depicted in FIG. 5. Treatment of v with 1-vinyl-2-piperidinone, followed by acid treatment, gives a compound of formula y. Reduction and N-methylation of y gives a compound of formula z. Compound z can be reduced to give pyrrolidinyl derivatives 22 and 23.

In the above described procedures, it may be convenient to protect a heteroatom in ring $R_e$ with an acceptable protecting group that can be removed at an appropriate time during the synthetic sequence. Suitable protecting groups as well as methods for their removal are known in the art (for example, see Greene, T. W.; Wutz, P. G. M. "Protecting Groups In Organic Synthesis" second edition, 1991, New York, John Wiley & sons, Inc).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically ;acceptable anion. Alkali metal (for example, sodium, potassium or lithium) or alkaline earth metal (for example calcium) salts of carboxylic acids can also be made.

The compound of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

The compounds of the invention can also be formulated for administration from a patch, e.g., as a patch that is similar to patches currently used in treating nicotine addiction.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to bind to nicotine receptors may be determined using pharmacological models which are well known to the art, or using Test A described below.

Test A

In vitro binding studies provide an indication of the affinity of a compound for a given receptor and are useful when viewed in the context with other various measures of functional activity. In vitro binding studies were performed with [$^3$H]cytisine (CYT) and $^{125}$I-$\alpha$-bungarotoxin ($\alpha$-BT) according to published procedures (L. A. Pabreza et al., 1990, 39, 9–12). These two ligands are known to bind preferentially to $\alpha_4\beta_2$ and $\alpha_7$ nicotine receptor subtypes, respectively. The binding data are provided in Table 1. Compound 1, shown in FIG. 9, displayed moderate affinity for the [$^3$H]cytisine binding site. In contrast, the threo isomer 6 was found to exhibit poor affinity for this binding site. The introduction of a hydroxy group at C6 led to a considerable loss of affinity for the [$^3$H]nicotine binding site. Similarly, N-demethylation resulted in a significant drop in affinity. Compound 4, and compound 9, with a C8-hydroxy group, demonstrated a 4-fold higher affinity than the corresponding unsubstituted compounds 1 and 6, while compounds 3 and 8, with a C7-hydroxy group, demonstrated at least 40-fold increased affinity compared to the respective unsubstitued compounds 1 and 6. Compounds 5 and 10, with a C8-hydroxy group, demonstrated increased affinity compared to the corresponding unsubstituted compounds 1 and 6. Compounds 13–15 demonstrated lower affinities compared to the corresponding unsubstituted compounds 1 and 6. Compounds 11 and 12 demonstrated increased affinity compared to the corresponding piperidinyl compounds 3 and 8.

For two of the diastereometric pairs, the erythro isomer (as assigned herein) displayed a 10-fold higher affinity than the threo isomer. The assignments for erythro and threo for the compounds disclosed herein were made based on NMR data. It is to be understood that these assignments could change if additional data becomes available. However, the invention includes both the erythro and threo isomers of the compounds of formula I disclosed herein. Accordingly, one specific group of compounds of formula I are compounds which are erythro (at the bond linking y and the substituent comprising $R_e$), and another specific group of compounds of formula I are compounds which are threo (at the bond linking y and the substituent comprising $R_e$.

Compounds 1–15 displayed poor affinity for the [$^{125}$I]-$\alpha$-bungarotoxin binding site. Since cytisine has been shown to bind preferentially to the $\alpha_4\beta_2$ nAChR subtype, this suggests that certain compounds of the invention bind selectively to the $\alpha_4\beta_2$ subtype. It is believed that a hydrogen bond acceptor is located within the vicinity of the pyridyl C5 position.

Compounds were tested in racemic form; it is possible that one enantiomer possesses significantly higher affinity than the racemate.

TABLE 1

Affinities of Compounds at $\alpha_4\beta_2$ and $\alpha_7$ Nicotine Receptors in Rat Brain

| Compound | (Ki-[3H]Cytisine (nM) | Ki-[125I]--BT (nM) |
|---|---|---|
| 1 | 6,200 ± 450 | >10,000 |
| 6 | 61,800 ± 5,010 | >10,000 |
| 2 | >10,000 | >10,000 |
| 7 | >10,000 | >10,000 |
| 3 | 93.4 ± 12 | >10,000 |
| 8 | 1,560 ± 250 | >10,000 |
| 4 | 1,620 ± 1,100 | NT** |
| 9 | 1,660 ± 1,450 | |
| 5 | >5,000 | NT |
| 10 | >5,000 | NT |
| 12 | 21.3 ± 9.4 | NT |
| 11 | 169.5 ± 36.4 | NT |
| (±)-13 | 7,906 | NT |
| (±)-14 | 8,947 ± 1,500 | NT |
| (±)-15 | >10,000 | NT |
| Cytisine | 2.78 ± 0.58 (0.9 ± 0.1)*[a] | |
| a-Bungarotoxin | NT | 14 |
| S-(−)-nicotine | 1.0 ± 0.02[b] | 4,000 ± 890[b] |
| ABT-089 (S) | 17 ± 2[b] | >10,000[b] |
| A-94224 (R) | 39 ± 4[b] | >10,000[b] |
| ABT-594 (S) | 0.037 ± 0.003[c] | 13,800 ± 390[c] |
| A-98593 (R) | 0.039 ± 0.003[c] | 4,620 ± 117[c] |

[a]*Assay performed at 4° C.;
[b]Sullivan et al., 1997;
[c]Donnelly-Roberts et al., 1998.
ABT-089 and A-94224 as well as ABT-594 and A-98593 are enantiomeric pairs.
**NT, not tested.

Representative compounds of the invention were also screened for binding to other receptors because structurally related compounds such as the aminotetralins, 7-OH-DPAT, 8-OH-DPAT, and 2-(aminomethyl)chromans have been shown to display high affinity for dopamine and serotonin receptors. Compounds 1, 5, 3, and 8 were tested for binding to dopamine D2 receptors and dopamine and serotonin transporter sites according to published methods such as described by S. M. Efange et al., *J. Med. Chem.*, 1997, 40, 3905–3914. All four compounds displayed a poor affinity for these sites, Ki>10 microMolar. With a Ki of 93 nM for the [$^3$H]cytisine binding site, the information in Table 1 suggests that compound 3 displays at the minimum 100-fold selectivity for the $\alpha_4\beta_2$ nicotinic acetylcholine receptor subtype.

The ability of a compound of the invention to act as a nicotine agonist in vivo may be determined using pharmacological models which are well known to the art, or using Test B described below.

Test B

Male Wistar rats weighing between 300 and 315 g were divided into two groups: CONTROL (n=3) and MEC (n=4). Animals in the CONTROL group were given a dose of compound 5–7a (200 µmol/kg, ip). Animals in the MEC group were administered a dose of mecamylamine (10 mg/kg, ip) fifteen minutes before administration of compound 3. All animals were observed for 1 hour and then at 17 hours post injection. In the CONTROL group, administration of compound 3 caused severe convulsions. Death occurred within 4 minutes post-injection.

Pretreatment with mecamylamine antagonized the lethal effects of compound 3 in three of the four animals. In two animals, no adverse effects were observed. Mild but short-lived spasms were observed in the third animal. The fourth animal expired within five minutes, probably due to a poor delivery of mecamyline.

These results, in combination with the results showing that the compounds possess poor affinity for dopamine receptors and monoamine transporters, indicate that compounds of the invention function as nicotine receptor agonists.

The ability of a compound of the invention to act as a nicotine agonist may also be determined using Tests C–G described below.

Test C

Measurement of $^{86}$Rb$^+$ Efflux in Rat Cortical Membranes

Preparation of synaptosomal fraction (P2). Rats were sacrificed by decapitation under diethyl ether anesthesia. The brains were removed quickly and dissected on an ice-cold platform to remove the cerebral cortices. The tissue was placed in 10 volumes (w/v) of ice-cold 0.32 M sucrose buffered to pH 7.5 with 5 mM HEPES and homogenized by hand with the aid of a Teflon-glass homogenizer. The homogenate was diluted to 25 volumes with ice-cold 0.32M sucrose, and centrifuged for 10 min at 1000 g at 4° C. The resulting supernatant was transferred to a separate tube and the pellet was resuspended in 10 volumes of homogenization medium, homogenized again and centrifuged for 10 min at 1000 g. The resulting supernatant was combined with the original supernatant and centrifuged for 20 min at 18,000 g to yield the P$_2$ pellet. The resulting (P$_2$) synaptosomal pellet was used for the $^{86}$Rb$^+$ efflux assay. Determination of $^{86}$Rb$^+$ efflux was performed as described by Marks et al, 1997 with some modifications introduced by Gattu et al, 1997.

$^{86}$Rb$^+$ efflux assay. Synaptosomes (250 mg protein/mL) were incubated for 30 min at 22° C. in 35 µL/sample of perfusion buffer containing 4 µCi of $^{86}$Rb$^+$(1 Ci/g) and 120.0 mM NaCl, 1.5 mM KCl, 2.0 mM CaCl$_2$, 1.0 mM MgCl$_2$, 50 mM HEPES, pH 7.5 and 20 mM D-glucose. Tetrodotoxin (50 nM) and CsCl$_2$ (5 mM) were added to the perfusion buffer to block (non-nicotinic) Na$^+$ channels and to reduce the basal efflux rate, respectively. The tissue was harvested and separated from the incubation medium by passing the mixture through 6-mm diameter glass fiber filters (Type GC 50, Adventec MFS, Inc., Pleasanton, Calif.) under gentle vacuum, followed by three washes with 0.6 mL incubation buffer at room temperature. The filters containing the $^{86}$Rb$^+$ loaded synaptosomes were placed on 13-mm glass fiber filters (Type GC 50, Adventec MFS, Inc., Pleasanton, Calif.) and perfused continuously at 22° C. After a wash period of 8 min, fractions were collected every 30 seconds for 2 min before exposure of the tissue to the nicotinic agonist and/or antagonist. Interaction of candidate molecules with nicotinic receptors occurs 3 min into the 10 min collection period. S-(-)-Nicotine (10 µM) was included in each experiment as control to account for variations between experiments. Radioactivity in the samples was measured by liquid scintillation counting.

The magnitude of the $^{86}$Rb$^+$ efflux was calculated by determining the increase in radioactivity above the baseline after stimulation of the tissue. The average base line underlying the peak was calculated by averaging the radioactivity present in the tubes immediately before and after the peak. Peak size was determined by subtracting the average baseline value from each fraction in the peak EC$_{50}$ values. The maximum response obtained for stimulation of $^{86}$Rb$^+$ efflux is calculated by use of Inplot (Graphpad, San Diego, Calif.). Data are analyzed by a two-way ANOVA with use of StatView II. The criterion of statistical significance was P<0.05.

Figure 9:
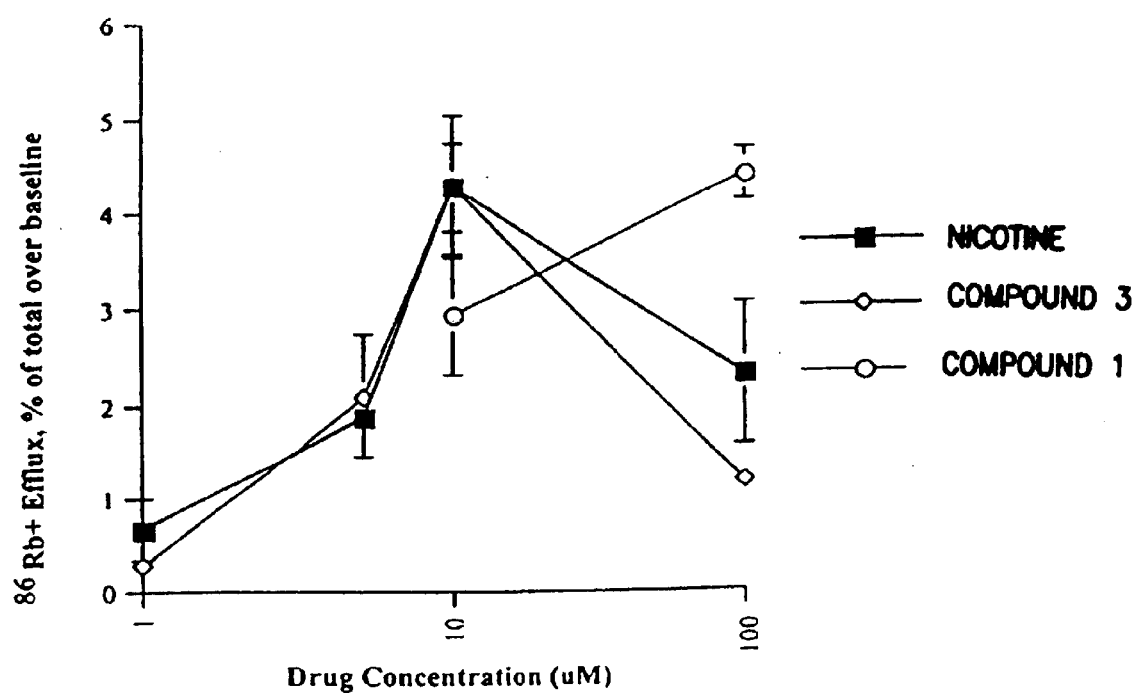
FIG. 9 illustrates data for drug induced Rubidium-86 release from rat cortical synaptosomes.

The nicotinic acetylcholine receptor (nAChR) is a ligand-gated ion channel. The binding of nicotine enhances ion flux across membrane. The ability to enhance ion flux across membranes therefore constitutes an important test of intrinsic efficacy. Drug-induced release of $^{86}$Rb$^+$ from rat cortical synaptosomes was determined by previously published procedures (Marks et al., 1993). This assay has been used to assess the ability of nicotine agonists to modulate ion fluxes across the plasma membrane. S-(-)-Nicotine and compound 3 were studied at four concentrations (1, 5, 10 and 100 µM), while compound 1 was studied at 10 and 100 µM due to its lower affinity for [$^3$H]cytisine binding sites (vide supra). At the concentrations studied, S-(-)-nicotine and racemic compound 3 displayed comparable potency in their ability to stimulate the release of $^{86}$Rb$^+$ from rat cortical synaptosomes (FIG. 9). In addition, the relative efficacy of racemic chromaperidine was comparable to that of nicotine. Consistent with its reduced affinity for [$^3$H]cytisine binding sites, compound 1 displayed lower potency in this assay. However, compound 1 could match the peak response of S-(-)-nicotine when tested at 100 µM. We conclude that compound 3 and compound 1 are effective activators of cholinergic channels.

Test D

Measurement of Striatal [$^3$H]Dopamine Release

Measurement of [$^3$H]dopamine uptake and efflux from striatal synaptosomes was performed as described by Rowell P. P. and Hillebrand J. A. (1994) (*J. Neurochem.* 63: 561–569), with some modifications described by Teng et al. (1997) (*J. Pharmacol Exp. Ther.* 280:1432–1444).

Striatal synaptosomes (160 mg protein/ml) were re-suspended in 15 mM HEPES buffer pH 7.5 containing 120 mM NaCl, 5 mM KCl, 1 mM MgCl$_2$, 2.5 mM CaCl$_2$, 1.25 mM NaH$_2$PO$_4$, 10 mM glucose, 10 µM pargyline, 10 µM ascorbic acid and pre-incubated for 10 min at 34° C. and loaded with 100 nM [$^3$H]dopamine for 15 min. The entire assay was performed in atmosphere of 95%O$_2$/5%CO$_2$. The tissue was harvested and separated from the incubation medium by filtration onto 1.2-mm diameter glass fiber filters (Type GC 50, Adventec MFS, Inc., Pleasanton, Calif.) under gentle vacuum, followed by two washes with 1.0 mL, incubation buffer at room temperature. The filters containing the [$^3$H]dopamine-loaded synaptosomes were placed on 2.1-mm glass fiber filters (Type GC 50, Adventec MFS, Inc., Pleasanton, Calif.) in a superfusion chamber and washed for 45 min at 0.8 ml/min with incubation buffer supplemented with 10 nM nomifensine, a dopamine re-uptake inhibitor. After the wash period, fractions were collected every 60 seconds for 10 min before exposure of the tissue to S-(–)-nicotine and study compounds. S-(–)-Nicotine and other study compounds were introduced for 5 min into a 30 min collection period. Radioactivity was measured by liquid scintillation counting. The magnitude of the [$^3$H]dopamine efflux was calculated by determining the increase in radioactivity above baseline following stimulation of the tissue. The average baseline underlying the peak was calculated by averaging the radioactivity present in the tubes before and after the peak. Peak size was determined by subtracting the average baseline value from each fraction in the peak. Data were then normalized to a fixed concentration of S-(–)-nicotine.

Figure 10:
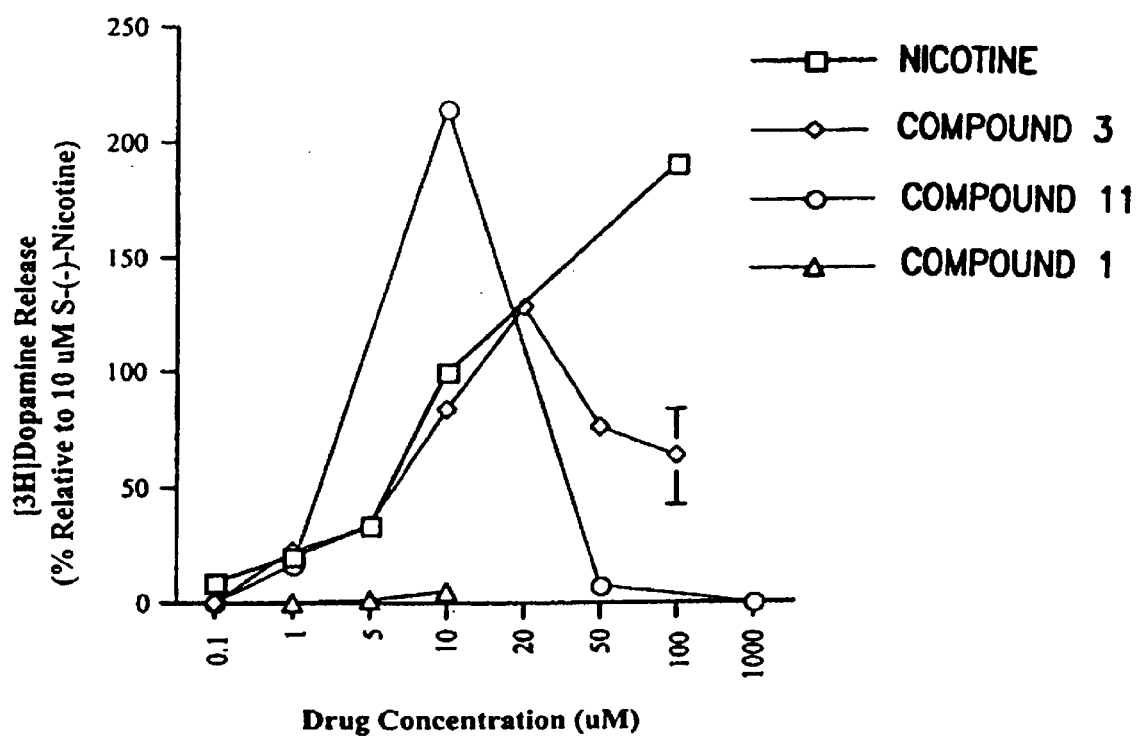
FIG. 10 illustrates data for drug induced release of [$^3$H] Dopamine from rat striatal synaptosomes.

The ability of nicotine and compounds 1, 3, and 11 to evoke the release of [$^3$H]dopamine from striatal synaptosomes was determined according to published procedures. Sullivan et al.(1997) (J. Pharmacol. Exptl. Ther. 283: 235–246). The viability of the synaptosomal preparation was confirmed by measuring K$^+$-evoked release of [$^3$H] dopamine. This was followed by measurement of nicotine-induced neurotransmitter efflux. The test compounds were evaluated at the end. Consistent with previous reports, nicotine induced release of [$^3$H]dopamine was dose-dependent. In agreement with its poor binding affinity, compound 1 failed to stimulate the release of [$^3$H]dopamine at doses of up to 10 μM (FIG. 10). On the other hand, compound 3 displayed dose-dependent stimulation of [$^3$H] dopamine release. The compound was equipotent with S-(–)-nicotine at 1, 5 and 10 μM. Higher doses of compound 3 were less effective, suggesting that peak effects are obtained at or near 10 μM. In deed, at 100 μM, compound 3 appeared to suppress K$^+$-evoked release of [$^3$H]dopamine. Compound 11 also stimulates the release of [$^3$H]dopamine from striatal synaptosomes. Compound 11 is considerably more effective than compound 3 or S-(–)-nicotine in this assay (FIG. 10), and would appear to be a good candidate for further evaluation in animal models of Parkinson's disease.

Test E
Measurement of [$^3$H]ACh Release

Drug-induced release of [$^3$H]ACh from hippocampal synaptosomes was measured as described by Sullivan et al. (1997). (J. Pharmacol. Exptl. Ther. 283: 235–246). The F4 synaptosomal fraction was washed with Kreb's buffer containing 118.5 mM NaCl, 25 mM NaHCO$_3$, 1.2 mM KCl, 1.2 mM KH$_2$PO$_4$, 2.5 mM CaCl$_2$, 2.5 mM MgCl$_2$, 10 mM glucose gassed with 95% O$_2$/5% CO$_2$ to pH 7.4 and re-suspended at 1 mg protein/mL. The synaptosomes were loaded with [$^3$H]choline by incubation with 0.8 μM [$^3$H] choline (2 Ci/mmol). Aliquots of the incubation mixture were then loaded into the perfusion chamber of a Brandell harvester and perfused with Kreb's buffer (37° C.) at a flow rate of 0.25 mL/min. Three-minute fractions were collected and measured for radioactivity. Drugs for study were administered as 20-s pulses. The [$^3$H]ACh release evoked by study compounds was normalized to (–)-nicotine-evoked release and to the total radioactivity accumulated by synaptosomes. Evoked release of [$^3$H]ACh from rat hippocampal synaptosomes was measured as the area under the peak above base release. The EC$_{50}$ value is determined by nonlinear least squares regression analysis.

Stimulation of dopamine release from the striatum is attributed to specific nAChR subtypes. Therefore, this assay measures the ability of a compound to stimulate specific nAChR subtypes. The assay provides an indication of the potential utility of the compound in the treatment of Parkinson's disease.

Figure 11:
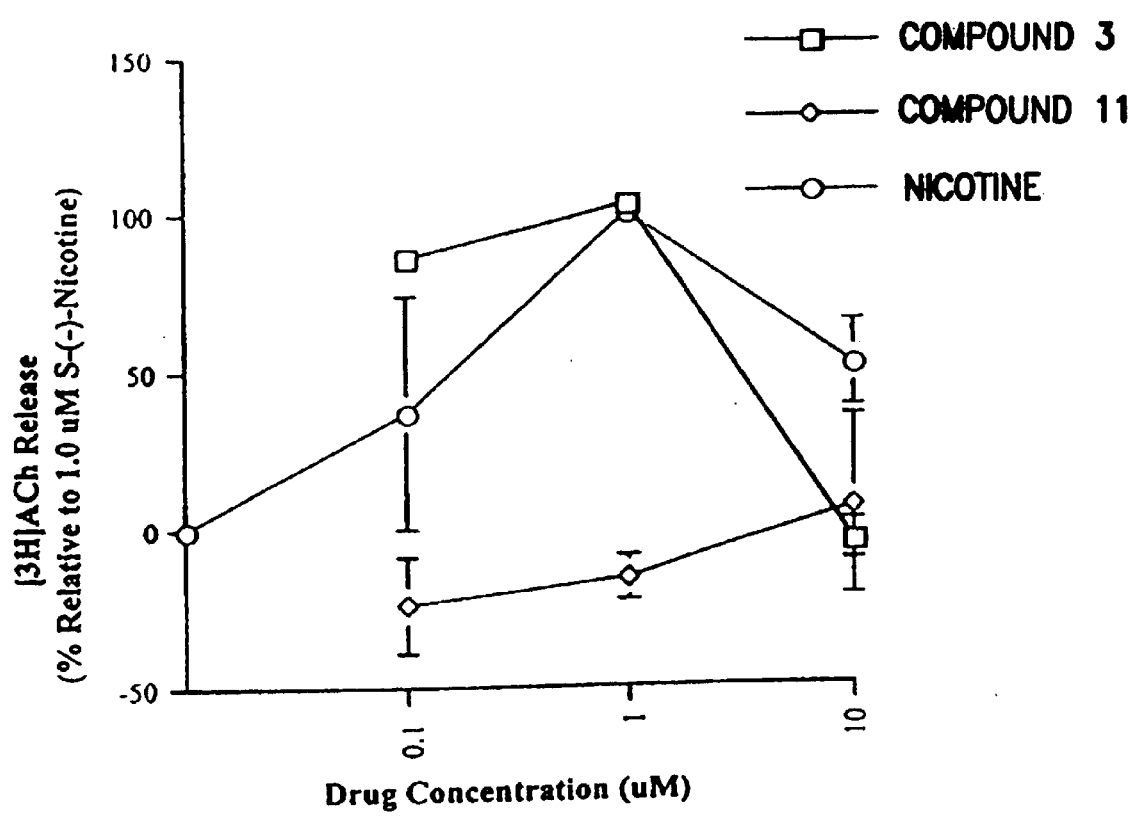
FIG. 11 illustrates data for drug induced release of [$^3$H] acetylcholine from rats.

Cholinergic hypofunction is one of the hallmarks of Alzheimer's disease (AD). Compounds that enhance the release of acetylcholine may be potentially useful in the management of AD. Chromaperidine can stimulate the release of [3H]ACh from cortical synaptosomes (FIG. 11). The potency of the racemate is lower than that of nicotine but the enantiomerically pure compound is expected to be as potent as nicotine. In contrast, compound 11 appears to have little intrinsic activity in this assay (FIG. 11). Chromaproline is thus highly selective for the dopaminergic system.

From the above data and the data in Table 2 below, it is clear that compound 11 selectively activates dopamine release in the striatum, while compound 3 is moderately selective for acetylcholine. Because the release of dopamine and acetylcholine has been attributed to distinct nAChR subtypes, it would appear that seemingly minor structure modification in this congeneric series can significantly alter subtype selectivity.

TABLE 2

| Bioassay | Compound 4 | Compound 11 |
|---|---|---|
| [$^3$H]Cytisine Binding | Moderate affinity | High affinity |
| $^{86}$Rb$^+$ efflux | High intrinsic activity | Not tested |
| [$^3$H]Dopamine release | Low to moderate activity | High intrinsic activity |
| [$^3$H]ACh release | High intrinsic activity | No intrinsic activity |

Test F
Behavioral Studies in Rats

The effects of racemic compound 11 on memory have been evaluated in ovariectomized female rats. Chromaproline hdrochloride was dissolved in physiological saline and delivered subcutaneously by osmotic mini pump (Alzet Model 2002) at the rate of 0.50 μL/hr to yield a dose of 1 μmol/kg/day. The dose and method of delivery were adapted from previous experiments with the nicotinic agonist ABT-089 (Decker et al, (1997) (JPET 283 247–258))).

Evaluation of the compound was carried out with an object recognition paradigm. This test has been used to probe some aspects of memory in monkeys (see also Decker et al, (1997) (*JPET* 283, 247–258)) and rodents (Ennaceur and Aggleton (1994)(*Expermental Brain Res.* 100, 85–92); Beck and Luine, (1999) (*Brain Res.* 830, 56–71) and has similarities to some human tests. Briefly, the test is composed of two phases: exploration and recognition. During the exploration phase, animals are placed in a field containing two identical objects and allowed to explore the field for 3 minutes. The time spent exploring each object is recorded. The animals are then removed from the field and one of the objects is replaced with a new (non-identical) object. After a delay (from 10 min to several hours), the animals are returned to the field and allowed once more to explore while the time spent exploring each object is recorded. The basis of the test is that rodents show more interest in novel objects. Therefore, during the recognition phase the animals will spend more time with the new object if they recognize it as being novel.

The current experiment used principally 2 groups of young adult ovariectomized rats: saline-treated controls (n=11) and compound 11 treated (n=10). Behavioral testing was initiated after 7 days of continuous infusion of the drug or saline. The results are pooled from three cohorts all of which showed the same results. Exploration times were not significantly different between the saline-treated controls and the drug-treated subjects.

To provide a frame of reference, a third group of animals (n–14) was treated with the acetylcholinesterase inhibitor ARICEPT™. The latter was delivered by osmotic mini pump at a dose of 1 mg/kg/day (approx. 2.5 mmol/kg/day).

Figure 12:
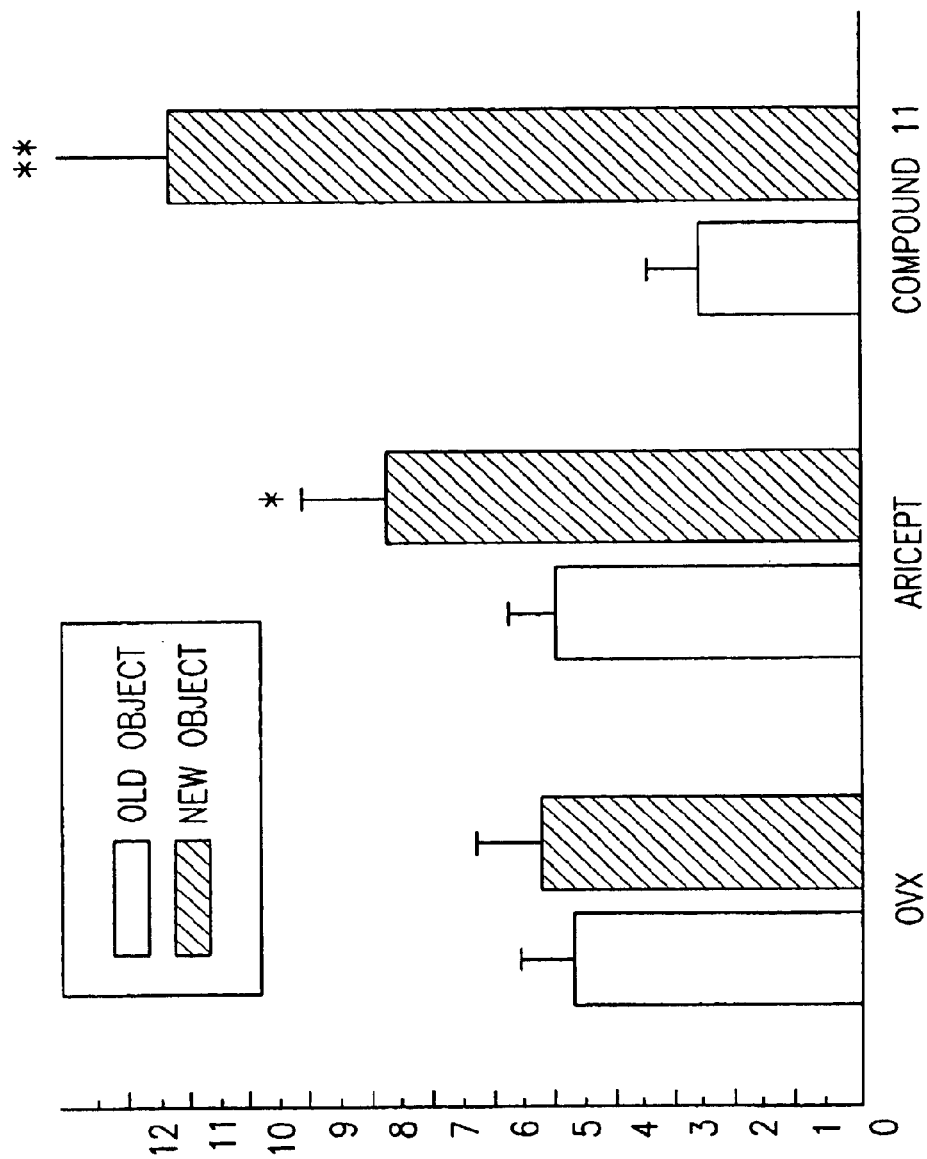
FIG. 12 illustrates data for memory experiments in rats.

The object recognition phase was initiated four hours after the exploration phase. In the saline-treated group, the time spent with the new object was essentially equal to the time spent with the old object (FIG. 12). With ARICEPT, the animals spent 60.1±5.4% (SEM) of the time exploring the new object. Moreover, with compound 11 the animals spent even more time (80.5±5% SEM) with the new object. The compound 11 group was significantly different from the saline-treated control and ARICEPT groups (p<0.05).

These experiments suggest that compounds of the invention are useful compounds for the treatment of memory disorders.

Test G
Effects of Compound 3 on Neuropathic Pain

The analgesic properties of compound 3 employed an established mouse model of neuropathic pain.

The Chung Model: Allodynia (abnormally increased sensitivity to normally innocuous stimuli) can be induced by surgical ligation of the L5 spinal nerve in halothane-anesthetized mice (Mogil, (1999)(Pain 80:67–82). The left paraspinal muscle is separated from the spinous processes at the L4–S2 levels and removed. The L6 transverse process is rendered accessible and then removed. Removal of the process permits visual identification of the L4–L5 spinal nerves. The L5 spinal nerve is tightly tied (ligated) with 6-0 silk thread distal to the dorsal root and proximal to the confluence of spinals nerves L4, L5, and L6 which comprises the sciatic nerve. After hemostasis is confirmed, the wound is sutured with 3-0 silk thread and the skin closed with sterile wound clips. The animals are fully mobile within thirty minutes of cessation of anesthetic. As a control, in a separate group of animals, a sham surgery identical to the above (but without nerve ligation) is performed. Nociception is evaluated by responsiveness to multiple applications (10 per hindpaw) of a single vF filament to the plantar surface of each hind paw. When the stimulus is of sufficient force, the mouse will lick, withdraw and/or shake the paw; this action represents the behavioral endpoint. In nerve-injured mice, a vF filament (#3.61) exerting 3.3 mN of force elicited 66±1.3% responsiveness on the paw ipsilateral to the injury. This level of response is sufficient to test compounds for dose-dependent inhibition of the response to mechanical sensation.

Inhibition of Tactile Sensitivity. Varying doses of the compounds are administered to test for inhibition of tactile sensitivity. Percent inhibition is determined relative to the mean number of paw withdrawals (PW) elicited by force and according to the following equation:

$$\% \text{ Inhibition} = \frac{(\# \text{ PW Pre-Drug} - \# \text{ of PW Post-Drug})}{\# \text{ PW Pre-Drug}}$$

Each mouse serves as its own control.

Three groups of animals were used for this experiment. Animals in each group received an intrathecal injection of physiological saline to assess the control response. Additionally, animals in group 1 (n=3), group 2 (n=4) and group 3 (n=4) received intrathecal injections of 30, 60 and 100 pmol compound 3 in physiological saline, respectively. The responses were assessed as described above.

Figure 13:
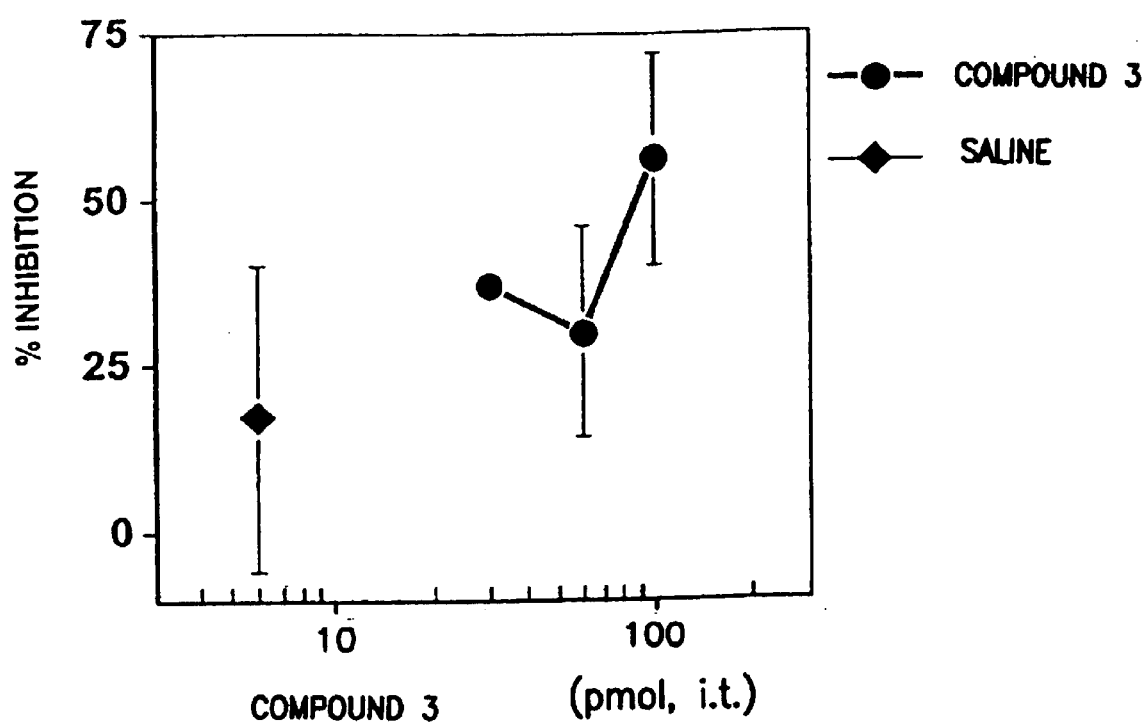
FIG. 13 illustrates the effect of compound (4) in inhibiting neuropathic pain behaviors in mice.

Compound 3 displayed dose-dependent inhibition of tactile sensitivity in nerve-injured mice. At the highest dose tested (100 pmol), the level of inhibition was 60% (FIG. 13). Compound 3 inhibits neuropathic pain in mice and is thus a potentially useful analgesic.

Representative compounds of the invention have been shown to be nicotine agonists. Accordingly, compounds of the invention may be useful as therapeutic agents for the treatment of disorders that are characterized by cholinergic dysfunction or that require nicotine receptor activation. Such disorders include but are not limited to, Alzheimer's disease, Parkinson's disease, schizophrenia, depression, attention deficit/hyperactivity disorder, neuropathic pain, ulcerative colitis, urinary incontinence, and olivopontocerebellar atrophy. Additionally, compounds of the invention may be useful as pharmacological tools for the further investigation of the actions of nicotine, nicotine agonists, and acetylcholine function. Compounds of the invention may also be useful as analgesics.

Certain compounds of formula I may also function as nicotine agonists. Assays useful to identify compounds possessing activity as nicotine agonists are known in the art. Nicotine antagonists may be useful as therapeutic agents for the treatment of diseases associated with the activity of nicotine receptors. Nicotine agonists may also be useful as pharmacological tools for the further investigation of the actions of nicotine, or may be useful to aid in the identification of compounds that function as nicotine agonists.

The invention will now be illustrated by the following non-limiting Examples wherein unless otherwise noted: synthetic intermediates were purchased from Aldrich Chemical Co. (Milwaukee, Wis.) and were used as received; tetrahydrofuran (TH) was distilled from sodium hydride immediately prior to use; dimethylacetamide and toluene were distilled from sodium shortly before use; other reagents and solvents were purchased as reagent grade and used without further purification; air-sensitive reactions were carried out under nitrogen; yields were not optimized; melting points were determined on a Haake-Buchler melting point apparatus and are uncorrected; $^1$H NMR spectra were recorded on a 300 MHz GE spectrometer; NMR spectra were referenced to the deuterium lock frequency of the spectrometer; with this condition, the chemical shifts (in ppm) of residual solvents are observed at 7.26 ($CHCl_3$), 4.78 ($CD_3OH$); preparative chromatography was performed on Harrison Research Chromatotron using Merck 60 PF254 silica gel or a preparative HPLC system (Rainin Instrument Co.) using a 41.1 mm id Dynamax silica gel column (delivering solvent at 80 mL/min); and analytical TLC was carried out on Analtech GHLf silica gel glass plates, and visualization was aided by UV and/or methanolic iodine.

EXAMPLE 1 erythro-2-(1-Methylpiperidin-2-yl)chroman (1)

A solution of the product from sub-part e below (6.5 g, 30.8 mmol) and iodomethane (26.2 g, 184.8 mmol) in anhydrous acetone was stirred at room temperature over 2 days. The resulting yellow precipitate was collected by filtration, washed with ether and dried to give 8.5 g (78%) of the pyridinium methiodide. The pyridinium methiodide was used without further purification.

Sodium borohydride (3.75 g, 99.1 mmol) was added portionwise over 30 minutes to a cooled (ice bath) stirring solution of the methiodide (7.0 g, 19.83 mmol) in methanol (100 mL). The reaction mixture was allowed to slowly come to room temperature and stirring was continued overnight. After 15 hours, the resulting solution was concentrated under reduced pressure to produce a colorless residue. The latter was partitioned between ethyl acetate (80 mL) and water (50 mL). After separation of the organic phase, the aqueous layer was re-extracted with ethyl acetate (2×80 mL). The organic extracts were combined, dried over anhydrous sodium sulfate and concentrated to provide 4.5 g (quant.) of the tetrahydropyridine.

A solution of the latter in methanol (40 mL) was treated with 10% Pd—C (150 mg) and hydrogenated on a Parr hydrogenator at 60 psi for 24 hours. The reaction mixture was filtered to remove the catalyst and other insoluble material, and the filtrate was concentrated to yield a mixture of the eurythro and threo isomers. Chromatographic separation by radial flow chromatography on silica gel (5% isopropyl alcohol-hexane plus 1% Et₃N) provided the individual erythro and threo diastereomers. In this system, the erythro isomer (the title compound) was found to elute before the threo isomer (the compound of Example 5). The title erythro isomer was prepared in 21% yield; mp 164–166° C. $^1$H NMR (CDCl₃) δ 1.00–3.10 (m, 16H, alkyl), 4.20–4.26 (m, 1H, C2-methine), 6.70–7.20 (m, 4H, phenyl). Elemental analysis calculated for $C_{15}H_{21}NO\cdot HCl$: C, 67.38; H, 8.30; N, 5.24. Found: C, 66.99; H, 8.27; N, 5.28.

a. trans-3-(2-Methoxyphenyl)-1-(2-pyridyl)propen-1-one. A solution of 2-acetylpyridine (6.06 g, 50 mmol) in EtOH (10 mL) was added dropwise over 30 minutes to a cold (ice bath) stirring solution of o-anisaldehyde (6.81 g, 50 mmol) in EtOH (100 mL) and 10% aq. NaOH (50 mL). After the addition, stirring and cooling were continued for 3 hours. The reaction mixture was allowed to come to room temperature and stirred overnight. After 15 hours at room temperature, the resulting mixture was filtered to give a yellow precipitate which was washed with 50% aq. EtOH and dried under reduced pressure at 50° C. to provide 9.9 g (83%) of the enone; $^1$H NMR (CDCl₃) δ 3.90 (s, 3H, methoxyl), 6.90–6.98 (m, 2H), 7.3–7.45 (m, 2H), 7.77–7.80 (m, 2H), 8.10–8.40 (m, 3H), 8.70 (d, 1H).

b. trans-3-(2-Methoxyphenyl)-1-(2pyridyl)propen-1-ol. Sodium Sodium borohydride (9.54 g, 0.25 mmol) was added portionwise over 30 minutes to a cooled (ice bath) stirring suspension of the compound from sub-part a, (14.73 g, 61.6 mmol) in anhydrous MeOH (200 mL). Complete dissolution was obtained at the end of the addition. The ice bath was removed and stirring was continued for 5 hours. Monitoring by TLC (20% acetone-hexane on silica gel) confirmed that the reaction had gone to completion. The reaction mixture was concentrated to a residue which was diluted with H₂O and extracted with $CH_2Cl_2$ (3×100 mL). The organic extracts were combined, dried over anhydrous $Na_2SO_4$ and concentrated to a yellow syrup (quant.). $^1$H NMR (CDCl₃) δ 3.75 (s, 3H, methoxyl), 5.38 (d, 1H, methine), 6.20–6.40 (q, 1H, vinyl), 6.8 (m, 2H), 7.15 (m, 2H), 7.30–7.40 (dd, 2H), 7.65 (m, 1H), 8.6 (d, 1H).

c. 3-(2-Methoxyphenyl)-1-(2-pyridyl)propan-1-ol. A solution of the alcohol from sub-part b (10.4 g, 43.3 mmol) in methanol (40 mL) was treated with 10% Pd-C (220 mg) and hydrogenated at 50 psi in a Parr hydrogenator for 24 hours. The mixture was filtered to remove the catalyst and the filtrate was passed though a short column of silica gel (50% acetone-hexane). Concentration of the eluent yield the product as a syrup (quant.). $^1$H NMR (CDCl₃) δ 1.70–2.30 (m, 2H, methylene), 2.50–3.00 (m, 2H, methylene), 3.60–3.95 (s, 3H, methoxyl), 4.60–4.90 (m, 1H, methine), 6.60–8.70 (m, 8H, aryl).

d. 3-(2-Hydroxyphenyl)-1-(2-pyridyl)propan-1-ol. Boron tribromide (7.79 g, 31.1 mmol) in methylene chloride (15 mL) was added dropwise over 30 minutes to a cooled (dry ice-acetone) stirring solution of the compound from sub-part c in dry methylene chloride (40 mL). The dry ice-acetone bath was maintained for an additional 30 minutes and subsequently replaced with a regular ice bath. Stirring and cooling were continued for 2.5 hours at which time the reaction was shown to be complete (TLC, silica gel, 50% acetone-hexane). The reaction mixture was cooled in a dry ice-acetone bath and carefully quenched with methanol (40 mL). The resulting solution was concentrated under reduced pressure and the residue was treated with a saturated solution of sodium bicarbonate (100 mL, aq.). Extraction of the mixture with methylene chloride (3×70 mL), followed by drying over anhydrous sodium sulfate and concentration provide the product as an orange syrup (3.4 g, quant.); $^1$H NMR (CDCl₃) δ 1.80–2.30 (m, 2H, methylene), 2.50–3.00 (m, 2H, methylene), 4.50–4.80 (m, 1H, methine), 5.00–6.40 (s, 2H, hydroxyl), 6.60–8.70 (m, 8H, aryl).

e. 2-(2-pyridyl)chroman. Triphenylphosphine (12.0 g, 45.8 mmol) and the compound from sub-part d (9.6 g, 39.5 mmol) were dissolved in dry THF (100 mL) and the solution was cooled in an ice bath. Diethyl azodicarboxylate (DEAD, 8.0 g, 46.0 mmol) was added dropwise under nitrogen, and the reaction mixture was allowed to come to room temperature. Stirring was continued at room temperature and the progress of the reaction was monitored by TLC (10% isopropyl alcohol-hexane, silica gel). The reaction was complete after one week. Solvent was removed under reduced pressure and the residue was passed through a short column of silica gel (50% acetone-hexane). The desired fractions were concentrated to a residue which solidified on cooling. The latter was triturated with diethyl ether, cooled, filtered and dried to provide the product as a white solid (6.5 g, 78%); $^1$H NMR (CDCl₃) δ 2.00–2.60 (m, 2H, methylene), 2.60–3.20 (m, 2H, methylene), 5.10–5.40 (m, 1H, methine), 6.60–8.70 (m, 8H, aryl).

EXAMPLE 2 erythro-5-Hydroxy-2-(1-methylpiperidin-2-yl) chroman (5)

The compound from sub-part e was subjected to a procedure similar to that described in Example 1. Separation of the erythro and threo isomers by chromatography gave the title compound; yield, 35%; mp 315–317° C. 1.10–2.90 (m, 16H, alkyl), 3.90–4.20 (m, 1H, C2-methine), 6.40–6.70 (m, 3H, aryl), 8.80–9.20 (s, 1H, phenol). $^1$H NMR (DMSO-d₆) δ 1.10–2.90 (m, 16H, alkyl), 3.90–4.20 (m, 1H, C2-methine), 6.40–6.70 (m, 3H, aryl), 8.80–9.20 (s, 1H, phenol). Elemental analysis calculated for $C_{15}H_{21}NO_2\cdot HCl$: C, 63.57; H, 7.83; N, 4.95. Found: C, 63.45; H, 7.77; N, 4.87.

a. trans-3-(2,3-Dimethoxyphenyl)-1-(2-pyridyl)propen-1-one. Using a procedure similar to that described in Example 1, sub-part a, except replacing the o-anisaldehyde used therein with 2,3-dimethoxybenzaldehyde the eneone was prepared: 73%; $^1$H NMR (CDCl₃) δ 3.80–4.00 (s, 6H, methoxyl), 6.90–7.00 (d, 1H, —CH=CH—CO), 6.90–7.20 (t, 1H, —CH=CH—CO), 7.20–8.80 (m, 7H, aryl).

b. trans-3-(2,3-Dimethoxyphenyl)-1-(2-pyridyl)propen-1-ol. The alcohol was prepared from the compound of sub-part a using a procedure similar to that described in Example 1, sub-part b; yield 95%; $^1$H NMR (CDCl$_3$) δ 3.80–4.00 (s, 6H, methoxyl), 4.90–5.10 (s, 1H, hydroxyl), 5.30–5.50 (m, 1H, methine-H), 6.20–6.40 (q, 1H, —CH=CH(OH)—), 6.80–6.90 (d, 1H, —CH=CH (OH)—), 6.90–8.80 (m, 7H, aryl).

c. 3-(2,3-Dimethoxyphenyl)-1-(2-pyridyl)propan-1-ol. The compound from sub-part b was hydrogenated using a procedure similar to that described in Example 1, sub-part c to give the saturated alcohol; yield, 95%; $^1$H NMR (CDCl$_3$) δ 1.80–2.90 (m, 4H, methylene), 3.60–3.90 (s, 6H, methoxyl), 4.20–4.70 (s, 1H, hydroxyl), 4.70–4.80 (m, 1H, methine), 6.70–8.60 (m, 7H, aryl).

d. 3-(2,3-Dihydroxyphenyl)-1-(2-pyridyl)propan-1-ol. The compound from sub-part c was treated with BBr$_3$ using a procedure similar to that described in Example 1, sub-part d to give the corresponding phenol; yield, 93%; $^1$H NMR (CDCl$_3$) δ 1.60–2.70 (m, 4H, methylene), 4.40–4.60 (m, 1H, methine), 5.20–5.60 (m, 1H, hydroxyl), 6.40–8.40 (m, 7H, aryl), 8.90–9.30 (s, 2H, phenol).

e. 8-Hydroxy-2-(2-pyridyl)chroman. The compound from sub-part d was subjected to a procedure similar to that described in Example 1, sub-part e to give the chroman; yield, 60%; $^1$H NMR (CDCl$_3$) 2.10–3.10 (m, 4H, methylene), 5.10–5.20 (q, 1H, methine), 6.00–6.20 (s, 1H, phenol), 6.80–8.80 (m, 7H, aryl).

EXAMPLE 3 erythro-7-Hydroxy-2-(1-methylpiperidin-2-yl) chroman (4)

The compound from sub-part e was subjected to a procedure similar to that described in Example 1. Separation of the erythro and threo isomers by chromatography gave the title compound; yield, 13%; mp (hydrochloride) 251–253° C. $^1$H NMR (DMSO-d$_6$) δ 1.00–3.60 (m, 16H, alkyl), 4.15–4.19 (m, 1H, C2-methine), 6.00–6.80 (m, 3H, phenyl), 9.00–9.10 (s, 1H, phenol). Element analysis calculated for C$_{15}$H$_{21}$NO$_2$.HCl: C, 63.57; H, 7.83; N, 4.95. Found: C, 63.26; H, 7.80; N, 4.87.

a. trans-3-(2,4-Dimethoxyphenyl)-1-(2-pyridyl)propen-1-one. Using a procedure similar to that described in Example 1, sub-part a, except replacing the o-anisaldehyde used therein with 2,4-dimethoxybenzaldehyde the eneone was prepared: 90%; $^1$H NMR (CDCl$_3$) δ 3.70–4.00 (s, 6H, methoxyl), 6.40–6.60 (m, 2H, vinyl), 7.20–8.80 (m, 7H, aryl).

b. trans-3-(2,3-Dimethoxyphenyl)-1-(2-pyridyl)propen-1-ol. The alcohol was prepared from the compound of sub-part a using a procedure similar to that described in Example 1, sub-part b; yield 83%; $^1$H NMR (CDCl$_3$) δ 3.60–4.00 (s, 6H, methoxyl), 4.70–5.00 (s, 1H, hydroxyl), 5.20–5.40 (s, 1H, methine-H), 6.20–6.60 (m, 2H, vinyl), 6.90–8.80 (m, 7H, aryl).

c. 3-(2,4-Dimethoxyphenyl)-1-(2-pyridyl)propan-1-ol. The compound from subpart b was hydrogenated using a procedure similar to that described in Example 1, sub-part c to give the saturated alcohol; yield, 96%; $^1$H NMR (CDCl$_3$) δ 1.80–2.90 (m, 4H, methylene), 3.60–4.00 (s, 6H, methoxyl), 4.00–4.60 (s, 1H, hydroxyl), 4.60–4.90 (m, 1H, methine), 6.30–8.70 (m, 7H, aryl).

d. 3-(2,4-Dihydroxyphenyl)-1-(2-pyridyl)propan-1-ol. The compound from sub-part c was treated with BBr$_3$ using a procedure similar to that described in Example 1, sub-part d to give the corresponding phenol; yield, 91%; $^1$H NMR (CDCl$_3$) δ 0.80–1.80 (m, 4H, methylene), 3.60–3.80 (m, 1H, hydroxyl), 4.30–4.50 (m, 1H, methine), 5.10–7.70 (m, 7H, aryl), 7.80–8.20 (s, 1H, phenolic-H).

e. 7-Hydroxy-2-(2-pyridyl)chroman. The compound from sub-part d was subjected to a procedure similar to that described in Example 1, sub-part e to give the chroman; yield, 84%; $^1$H NMR (CDCl$_3$+DMSO-d$_6$) δ 1.80–2.80 (m, 4H, methylene),4.90–5.10 (m, 1H, methine), 6.20–8.60 (m, 7H, aryl), 8.90–9.00 (s, 1H, phenol). The free base was converted to the corresponding hydrochloride by dissolving in cold methanolic HCl, concentration of the solution and recrystallization from ethyl alcohol. Elemental analysis calculated for C$_{14}$H$_{13}$NO.HCl: C, 63.86; H, 5.36; N, 5.32. Found: C, 63.64; H, 5.38; N, 5.27.

EXAMPLE 4 erythro-6-Hydroxy-2-(1-methylpiperidin-2-yl) chroman (3)

The compound from subpart e was subjected to a procedure similar to that described in Example 1. Separation of the erythro and threo isomers by chromatography gave the title compound; yield, 10%; mp 289–291° C. $^1$H NMR (DMSO-d$_6$) δ 1.50–4.00 (m, 16H, alkyl), 4.30–4.40 (m, 1H, C2-methine), 6.40–6.80 (m, 3H, aryl), 8.80–9.00 (s, 1H, phenol), 9.80–10.80 (br s, 1H, acid H). Elemental analysis calculated for C$_{15}$H$_{21}$NO$_2$.HCl: C, 63.57: H, 7.83; N, 4.95. Found: C, 63.41; H, 7.81; N, 4.97.

a. trans-3-(2,5-Dimethoxyphenyl)-1-(2-pyridyl)propen-1-one. Using a procedure similar to that described in Example 1, sub-part a, except replacing the o-anisaldehyde used therein with 2,5-dimethoxybenzaldehyde the eneone was prepared: 77%; $^1$H NMR (DMSO-d$_6$) δ 3.60–4.00 (s, 6H, methoxyl), 6.90–7.10 (m, 2H, vinyl), 7.2–8.80 (m, 7H, aryl).

b. trans-3-(2,5-Dimethoxyphenyl)-1-(2-pyridyl)propen-1-ol. The alcohol was prepared from the compound of sub-part a using a procedure similar to that described in Example 1, sub-part b; yield 89%; $^1$H NMR (CDCl$_3$) δ 3.60–3.90 (s, 6H, methoxyl), 4.90–5.10 (s, 1H, hydroxyl), 5.30–5.40 (d, 1H, methine-H), 6.20–6.40 (m, 2H, vinyl), 6.70–8.80 (m, 7H, aryl).

c. 3-(2,5-Dimethoxyphenyl)-1-(2-pyridyl)propan-1-ol. The compound from sub-part b was hydrogenated using a procedure similar to that described in Example 1, sub-part c to give the saturated alcohol; yield, 96%; $^1$H NMR (CDCl$_3$) δ 1.80–2.90 (m, 4H, methylene), 3.60–3.80 (s, 6H, methoxyl), 4.00–4.50 (s, 1H, hydroxyl), 4.70–4.80 (m, 1H, methine), 6.60–8.60 (m, 7H, aryl).

d. 3-(2,5-Dihydroxyphenyl)-1-(2-pyridyl)propan-1-ol. The compound from sub-part c was treated with BBr$_3$ using a procedure similar to that described in Example 1, sub-part d to give the corresponding phenol; yield, quantitative; $^1$H NMR (CDCl$_3$) δ 1.60–2.80 (m, 4H, methylene), 4.40–4.60 (m, 1H, methine), 5.30–5.40 (m, 1H, hydroxyl), 6.20–8.40 (m, 7H, aryl) 8.30–8.50 (s, 2H, phenolic).

e. 6-Hydroxy-2-(2-pyridyl)chroman. The compound from sub-part d was subjected to a procedure similar to that described in Example 1, sub-part e to give the chroman; yield, 60%; $^1$H NMR (CDCl$_3$) δ 1.90–3.00 (m, 4H, methylene), 5.10–5.20 (m, 1H, methine), 6.50–7.80 (m, 7H, aryl), 8.50–8.70 (s, 1H, phenol).

EXAMPLE 5 erythro-5-Hydroxy-2-(1-methylpiperidin-2-yl) chroman (2)

The compound from subpart e was subjected to a procedure similar to that described in Example 1. Separation of the erythro and threo isomers by chromatography gave the title compound; yield, 11%; mp 287–289° C. $^1$H NMR (DMSO-$d_6$) δ 1.00–3.10 (m, 16H), 4.20–4.30 (m, 1H), 6.25–7.00 (m, 4H). Elemental analysis calculated for $C_{15}H_{21}NO_2 \cdot HCl$: C, 63.57; H, 7.83; N, 4.95. Found: C, 63.55; H, 7.86; N, 4.92.

a. trans-3-(2,6-Dimethoxyphenyl)-1-(2-pyridyl)propen-1-one. Using a procedure similar to that described in Example 1, sub-part a, except replacing the o-anisaldehyde used therein with 2,6-dimethoxybenzaldehyde (5.70 g, 34.3 mmol) and 2-acetylpyridine (4.28 g, 35.3 mmol) the eneone was prepared 94%; $^1$H NMR (CDCl$_3$) δ 3.90–4.00 (s, 6H, methoxyl), 6.50–6.60 (m, 2H, vinyl), 7.20–8.80 (m, 7H, aryl).

b. trans-3-(2,6-Dimethoxyphenyl)-1-(2-pyridyl)propen-1-ol. The alcohol was prepared from the compound of sub-part a using a procedure similar to that described in Example 1, sub-part b; yield 99%. $^1$H NMR (CDCl$_3$) d 3.70–3.90 (s, 6H), 4.40–5.00 (s, 1H), 5.30–5.40 (d, 1H), 6.50–6.60 (d, 2H), 6.70–8.60 (m, 7H).

c. 3-(2,6-Dimethoxyphenyl)-1-(2-pyridyl)propan-1-ol. The compound from sub-part b was hydrogenated using a procedure similar to that described in Example 1, sub-part c to give the saturated alcohol; yield, 98.8%. $^1$H NMR (CDCl$_3$) δ 1.80–2.90 (m, 4H), 3.70–3.90 (s, 6H), 4.00–4.60 (s, 1H), 4.60–4.80 (m, 1H), 6.50–8.80 (m, 7H).

d. 3-(2,6-Dihydroxyphenyl)-1-(2-pyridyl)propan-1-ol. The compound from sub-part c was treated with BBr$_3$ using a procedure similar to that described in Example 1, subpart d to give the corresponding phenol; yield, 89%. $^1$H NMR (CDCl$_3$+DMSO-$d_6$) δ 1.80–2.75 (m, 4H), 4.30–4.40 (m, 1H), 4.50–5.50 (m, 1H), 6.10–9.50 (m, 9H).

e. 5-Hydroxy-2-(2-pyridyl)chroman. The compound from sub-part d was subjected to a procedure similar to that described in Example 1, sub-part e to give the chroman; yield, 56%. $^1$H NMR (CDCl$_3$) δ 1.90–2.90 (m, 4H), 5.10–5.30 (m, 1H), 6.40–8.80 (m, 8H). The free base was converted to the hydrochloride with cold methanolic HCl and recrystallized from absolute ethanol; mp 246–248° C. Elemental analysis calculated for $C_{14}H_{13}NO \cdot HCl$: C, 63.86; H, 5.36; N, 5.32. Found: C, 66.74; H, 5.33; N, 5.30.

EXAMPLE 6 threo-5-Hydroxy-2-(1-methylpiperidin-2-yl)chroman (10)

The title compound was isolated from the chromatography described in Example 2; yield, 15%; mp 291–293° C. $^1$H NMR (DMSO-$d_6$) δ 1.20–3.10 (m, 16H, alkyl), 4.00–4.20 (m, 1H, C2-methine), 6.40–6.60 (m, 3H, aryl), 7.00–8.20 (s, 1H, phenol). Elemental analysis calculated for $C_{15}H_{21}NO_2 \cdot HCl$: C, 63.57; H, 7.83; N, 4.95. Found: C, 62.94; H, 7.75; N, 4.83.

EXAMPLE 7 threo-7-Hydroxy-2-(1-methylpiperidin-2-yl)chroman (9)

The title compound was isolated from the chromatography described in Example 3; yield, 66%; mp (hydrochloride) 265–267° C. $^1$H NMR (CDCl$_3$) δ (free base) 1.00–3.60 (m, 16H, alkyl), 3.98–4.10 (m, 1H, C$_2$-methine), 6.00–6.80 (m, 3H, aryl), 9.00–9.10 (s, 1H, phenol). Elemental analysis calculated for $C_{15}H_{21}NO_2 \cdot HCl$: C, 63.57; H, 7.83; N, 4.95. Found: C, 63.31; H, 7.78; N, 4.95.

EXAMPLE 8 threo-7-Hydroxy-2-(1-methylpiperidin-2-yl)chroman (7)

The title compound was isolated from the chromatography described in Example 3; yield, 66%; mp (hydrochloride) 265–267° C. $^1$H NMR (CDCl$_3$) δ (free base) 1.00–3.60 (m, 16H, alkyl), 3.98–4.10 (m, 1H, C2-methine), 6.00–6.80 (m, 3H, aryl), 9.00–9.10 (s, 1H, phenol). Elemental analysis calculated for $C_{15}H_{21}NO_2 \cdot HCl$: C, 63.57; H, 7.83; N, 4.95. Found: C, 63.31; H, 7.78; N, 4.95.

EXAMPLE 9 threo-6-Hydroxy-2-(1-methylpiperidin-2-yl)chroman (8)

The title compound was isolated from the chromatography described in Example 4; yield, 60%; mp 286–288° C. $^1$H NMR (DMSO-$d_6$) δ 1.30–3.60 (m, 16H, alkyl), 6.40–6.80 (m, 3H, aryl), 8.80–9.00 (s, 1H, phenol), 9.80–10.80 (br s, 1H, acid H). Elemental analysis calculated for $C_{15}H_{21}NO_2 \cdot HCl$: C, 63.57; H, 7.83; N, 4.95. Found: C, 63.66; H, 7.83; N, 4.99.

EXAMPLE 10 threo-2-(1-Methylpiperidin-2-yl)chroman (6)

The title compound was isolated from the chromatography described in Example 1; yield, 55%; mp 202–204° C. $^1$H NMR (CDCl$_3$) δ 1.20–3.10 (m, 16H, alkyl), 4.27–4.34 (m, 1H, C2-methine), 6.70–7.20 (m, 4H, phenyl). Elemental analysis calculated for $C_{15}H_{21}NO \cdot HCl$: C, 67.38; H, 8.30; N, 5.24. Found: C, 67.01; H, 8.14; N, 5.18.

EXAMPLE 11

1-Methyl-2-(2-indenyl)methylpiperidine hydrochloride (13)

Iodomethane (9.5 g, 67.3 mmol) was added to solution of (E)-2-(2'-pyridylmethylene-1-indanol from sub-part b below (3.0 g, 13.5 mmol) and the resulting mixture was stirred maintained at 35° C. After 3 days, the reaction mixture was filtered and the precipitate was washed with diethyl ether and dried to yield 3.0 g (61%) of the pyridinium methiodide.

The material was dissolved in methanol (60 mL) and the resulting solution was cooled in an ice bath. Sodium borohydride (1.55 g, 41.1 mmol) was added portionwise over 30 minutes with continued cooling. The reaction mixture was allowed to slowly come to room temperature and stirring was continued overnight. After 16 hours, the reaction mixture was concentrated to a residue. The latter was partitioned between water (50 mL) and ethyl acetate (80 mL). Following separation of the layers, the aq. layer was re-extracted with ethyl acetate (2×80 mL), the organic extracts were dried over anhydrous Na$_2$SO$_4$ and concentrated in vacuo to yield 1.9 g (96%) of the crude mixture of diastereomeric tetrahydropyridines (k$_1$ and k$_2$ wherein R=H). The latter (1.5 g, 7.5 mmol) was dissolved in methanol (20 mL) and the solution was treated with 10% Pd—C (250 g). The resulting mixture was hydrogenated at 70 psi for 4 hours. The mixture was filtered to remove the catalyst and the filtrate was concentrated to yield a residue. The residue was passed through a short column of silica gel (50% acetone-hexane). Concentration of the eluent provided 1.4 g (91%) of the diastereomeric piperidines (k$_3$) $^1$H NMR (CDCl$_3$) δ 1.00–2.50 (m, 12H), 2.60–3.00 (m, 3H), 3.40–3.70 (m, 2H), 4.50–4.70 (m, 1H), 4.70–5.30 (m, 1H), 7.00–7.70 (m, 9H).

A solution of the diastereomeric piperidines (0.7 g, 2.86 mmol) in freshly distilled toluene (60 mL) was heated to 110° C. Solid p-toluenesulfonic acid mono hydrate (0.7 g, 3.70 mmol) was added in one lot and the mixture was refluxed until TLC (30% acetone-hexane, silica gel) indicated completion of the reaction (1 hour). The reaction mixture was allowed to cool to room temperature and subsequently treated 5% aq. NaOH (80 mL). The resulting mixture was extracted with ethyl acetate (3×60 mL). The combined organic extracts were dried over anhydrous sodium sulfate and concentrated to a residue which was purified on a short column of silica gel (30% acetone-hexane+1% Et$_3$N) to yield 200 mg (31%) of 18a. $^1$H NMR (CDCl$_3$) δ 1.20–2.70 (m, 12H), 2.80–3.00 (m, 2H), 3.30–3.40 (s, 2H), 6.50–6.70 (s, 1H), 7.10–7.50 (m, 4H). The hydrochloride was obtained by dissolving the free base in cold methanolic HCl, concentrating the resulting solution and recrystallizing from ethanol; mp 192–194° C. Elemental analysis calculated for $C_{16}H_{21}N$·HCl: C, 72.96; H, 8.43; N, 5.32. Found: C, 72.45; H, 8.44; N, 5.22.

The intermediate (E)-2-(2'-pyridylmethylene-1-indanol was prepared as follows.

a. (E)-2-(2'-pyridylmethylene)-1-indanone (h, wherein R=H). 2-Pyridinecarboxaldehyde (5.5 g, 51.3 mmol) and 1-indanone (6.5 g, 49.2 mmol) were dissolved in ethanol (150 mL) and the solution was cooled in an ice bath. A cold solution of KOH (11.0 g) in water (10 mL) was added dropwise over 30 minutes. Stirring and cooling were continued for 1 hour at which time the precipitated product was collected by filtration, washed with 50% aq. ethanol (10 mL) and dried to give a chromatographically homogeneous (30% acetone-hexane, silica gel) yellow solid (5.5 g, 50%). $^1$H NMR (CDCl$_3$) δ 4.20–4.21 (d, 2H, methylene), 7.20–8.80 (m, 9H, aryl).

b. (E)-2-(2'-pyridylmethylene-1-indanol (i, wherein R=H). Sodium borohydride was added portionwise over 1 hour to a cooled (ice bath) stirring solution of the compound from sub-part a (5.0 g, 22.6 mmol). The reaction mixture was allowed to slowly come to room temperature and stirred overnight. After 15 hours, the reaction mixture was concentrated under reduced pressure. The resulting residue was diluted with water and the resulting mixture was extracted with ethyl acetate (4×100 mL). The organic extracts were combined, dried over anhydrous sodium sulfate and concentrated to give 4.8 g (95%) of the product. The material was used without further purification. $^1$H NMR (CDCl$_3$) δ 2.60–3.30 (m, 2H, methylene), 3.90–4.30 (d, 1H, methine), 7.00–8.60 (m, 9H, aryl & vinyl).

EXAMPLE 12

1-Methyl-2-(6-methoxyinden-2-yl)methylpiperidine hydrochloride (14)

Using a procedure similar to that described in Example 11 except replacing the (E)-2-(2'-pyridylmethylene-1-indanol used therein with (E)-6-methoxy-2-(2'-pyridylmethylene-1-indanol, the title compound was prepared; yield (4 steps), 12%; mp (hydrochloride) 156–158° C. $^1$H NMR (CDCl$_3$) δ 1.20–3.20 (m, 14H), 3.20–3.40 (m, 2H), 3.70–3.90 (s, 3H), 5.60–5.80 (s, 1H), 6.40–7.30 (m, 3H). Elemental analysis calculated for $C_{15}H_{21}NO_2$·HCl: C, 69.59; H, 8.25; N, 4.78. Found: C, 69.25; H, 8.17; N, 4.73.

The intermediate (E)-6-methoxy-2-(2'-pyridylmethylene-1-indanol was prepared as follows.

a. (E)-6-methoxy-2-(2'-pyridylmethylene)-1-indanone (FIG. 5, h, wherein R=6-methoxy). Using a procedure similar to that described in Example 9, sub-part a, except replacing the 1-indanone used therein with 6-methoxyindanone, the methylene compound was prepared; yield, 63%; $^1$H NMR (CDCl$_3$) δ 3.80–4.00 (s, 3H), 4.10–4.30 (d, 2H), 7.10–8.80 (m, 8H).

b. (E)-6-methoxy-2-(2-pyridylmethylene-1-indanol (FIG. 5, i, wherein R=6-methoxy). Using a procedure similar to that described in Example 9, sub-part b, except replacing the (E)-2-(2'-pyridylmethylene)-1-indanone used therein with the (E)-6-methoxy-2-(2'-pyridylmethylene)-1-indanone prepared in sub-part a, the alcohol was prepared; yield, 85%; $^1$H NMR (CDCl$_3$) δ 3.70–3.90 (s, 3H), 3.90–4.20 (m, 2H), 5.60–5.70 (s, 1H), 6.80–8.60 (m, 8H).

EXAMPLE 13

1-Methyl-2-(6-hydroxyinden-2-yl)methylpiperidine hydrochloride (15)

1-Methyl-2-(6-methoxyinden-2-yl)methylpiperidine (14) was subjected to a procedure similar to that described in Example 1, sub-part d to provide 1-methyl-2-(6-hydroxyinden-2-yl)methylpiperidine. Formation of the hydrochloride gave the title compound; yield, quantitative; mp 217–219° C. $^1$H NMR (CDCl$_3$) δ 1.10–3.10 (m, 14H), 3.10–3.40 (m, 2H), 5.60–5.80 (s, 1H), 6.40–7.30 (m, 3H), 7.90–8.60 (s, 1H). Elemental analysis calculated for $C_{15}H_{21}NO_2$·HCl: C, 68.78; H, 7.94; N, 5.02. Found: C, 68.56; H, 8.21; N, 4.75.

EXAMPLE 14 threo-7-Hydroxy-2-(1-methylpyrrolidin-2-yl) chroman (12)

Erythro-3-(2,4-Dihydroxyphenyl)-1-(1-methylpyrrolidin-2-yl)propan-1-ol (2.6 g, 10.4 mmol) and triphenylphosphine (2.9 g, 11.1 mmol) were added to a dried flask containing 150 mL of freshly distilled 1,4-dioxane and 30 mL of dry DMF, and the resulting solution was cooled in an ice bath. Diethyl azodicarboxylate (2.0 g, 11.5 mmol) was added dropwise under nitrogen. Following the addition, the reaction temperature was slowly raised to room temperature over 2 hours. Stirring was then continued overnight. After 16 hours, the reaction was found to be incomplete. The mixture was refluxed for 20 hours, cooled and concentrated to remove excess solvent. The residue was redissolved in ethyl acetate (20 mL) and chilled to precipitate triphenylphosphine oxide. The latter was removed by filtration and the filtrate was concentrated to a residue which was chromatographed on a silica gel column (30% acetone-hexane) to give the crude product. Further purification of the latter was obtained by radial flow chromatography on silica gel (30% THF-hexane) to yield 0.7 g (31%) of 25 as the free base; EIMS (FAB) calcd for $C_{14}H_{19}NO_2$ m/z 233.1416; found, 234.1481 (M+H)$^+$, 100%. The corresponding hydrochloride was obtained by dissolving the free base in cold methanolic HCl. After solvent removal, the hydrochloride was crystallized from absolute ethanol as a white solid: mp (hydrochloride) 241–243° C.; $^1$H NMR [free base] (CDCl$_3$) d 1.60–3.80 (m, 13H), 3.10–3.30 (m, 1H), 4.00–4.10 (m, 1H), 6.30–6.90 (m, 3H). Elemental analysis calculated for $C_{14}H_{19}NO_2$·HCl: C, 62.43; H, 7.49; N, 5.20. Found: C, 62.21; H, 7.46; N, 5.15.

Erythro-3-(2,4-Dihydroxyphenyl)-1-(1-methylpyrrolidin-2-yl)propan -1-ol was prepared as follows.

a. trans-3-(2,4-Dimethoxyphenyl)-1-(1-butoxycarbonyl-pyrrolidin-2-yl)propen-2-one. A cold solution of 10% aq. NaOH (100 mL) was added dropwise to a cold stirring solution of 2,4-dimethoxybenzaldehyde (10.0 g, 60 mmol) and BOC-protected 2-acetyl pyrrolidine (14.0 g, 66 mmol). Upon completion of the addition, the reaction mixture was stirred for 20 hours and monitored by tlc (30% ethyl acetate-hexane, silica gel). After 20 hours, the reaction mixture was diluted with and extracted with ethyl acetate (4×60 mL). The combined organic extracts were washed consecutively with 0.6N HCl (volume) and saturated sodium bicarbonate, dried over anhydrous $Na_2SO_4$ and concentrated under reduced pressure to yield the crude product. The latter was purified by column chromatography on silica gel (10% ethyl acetate) to provide 15 g (69%) of trans-3-(2,4-Dimethoxyphenyl)-1-(1-butoxycarbonylpyrrolidin-2-yl)propen-2-one; 1H NMR ($CDCl_3$) δ 1.20–1.50 (d, 9H, tert-butyl), 1.50–3.70 (m, 7H, pyrrolidyl), 3.80–3.90 (d, 6H, methoxyl), 6.40–8.00 (m, 5H, aryl & vinyl). EIMS (FAB) calcd for $C_{20}H_{27}NO_5$ m/z 361.1889; found, 362.1998 $(M+H)^+$, 32%.

b. erythro-3-(2,4-Dimethoxyphenyl)-1-(1-methylpyrrolidin-2-yl)propan-1-ol & threo-3-(2,4-Dinethoxyphenyl)-1-(1-methylpyrrolidin-2-yl)propan-1ol. A solution of trans-3-(2,4-Dimethoxyphenyl)-1-(1-butoxycarbonylpyrrolidin-2-yl)propen-2-one (15.0 g, 41.6 mmol) in 10 mL of freshly distilled THF was added under nitrogen to a cold (ice bath) stirring suspension of $LiAlH_4$ (20.0 g, 527 mmol). The mixture was heated slowly to reflux and maintained in this condition overnight. The reaction mixture was then cooled in an ice bath, diluted with THF (200 mL) and quenched by careful dropwise addition of water (20 mL) and 15% NaOH (60 mL), consecutively. The resulting mixture was stirred for 1 hour, and filtered to remove a white precipitate. The latter was washed EtOAc (200 mL), and set aside. The filtrate was dried over anhydrous $Na_2SO_4$ and concentrated under reduced pressure to provide a crude mixture of erythro-3-(2,4-Dimethoxyphenyl)-1-(1-methylpyrrolidin-2-yl)propan-1-ol and threo-3-(2,4-Dimethoxyphenyl)-1-(1-methylpyrrolidin-2-yl)propan-1-ol. The latter were separated by silica gel chromatography with 30% THF-hexane as mobile phase. Under these conditions, compound erythro-3-(2,4-Dimethoxyphenyl)-1-(1-methylpyrrolidin-2-yl)propan-1-ol eluted first. erythro-3-(2,4-Dimethoxyphenyl)-1-(1-methylpyrrolidin-2-yl) propan-1-ol: Yield, 4.6 g (79%); $^1$H NMR ($CDCl_3$) δ 1.50–3.30 (m, 15H), 3.70–3.80 (m, 1H), 3.80–3.90(s, 6H), 6.40–7.20(m, 3H). threo-3-(2,4-Dimethoxyphenyl)-1-(1-methylpyrrolidin-2-yl)propan-1-ol: Yield, 3.9 g (69%); $^1$H NMR ($CDCl_3$) δ 1.45–3.30 (m, 16H), 3.70–3.00 (s, 6H), 6.40–7.20 (m, 3H). EIMS (FAB) calcd for $C_{16}H_{25}NO_3$ m/z 279.1834; found, 280.1938 $(M+H)^+$, 100%.

c. erythro-3-(2,4-Dihydroxyphenyl)-1-(1-methylpyrrolidin-2-yl)propan-1-ol. Erythro-3-(2,4-Dimethoxyphenyl)-1-(1-methylpyrrolidin-2-yl)propan-1-ol (6.0 g, 21.5 mmol) was dissolved in 250 mL of methylene chloride and the resulting solution was cooled in a Dry Ice-acetone bath and stirred under nitrogen. A solution of boron tribromide (6.0 mL, 63.9 mmol) in 20 mL of dry methylene chloride was then added dropwise over 30 min. The Dry Ice-acetone bath was replaced with an ice bath and stirring was continued overnight while the reaction temperature was allowed to rise slowly to room temperature. After 20 hours, the reaction mixture was cooled in Dry Ice-acetone bath and the reaction was quenched by careful addition of methanol (10 mL). The pH of the solution was adjusted to 9–11 with aq. NaOH and the layers were separated. The aq. layer was further extracted with EtOAc (4×100 mL) and set aside. The organic extracts were combined, dried over anhydrous $NaSO_4$ and concentrated under reduced pressure to yield 2.6 g (48%) of erythro-3-(2,4-Dihydroxyphenyl)-1-(1-methylpyrrolidin-2-yl)propan-1-ol. $^1$H NMR (Acetone-$d_6$+DMSO-$d_6$) d 1.40–3.30 (m, 14H), 3.60–3.80 (m, 1H), d 5.90–6.70 (m, 3H).

EXAMPLE 15 erythro-7-Hydroxy-2-(1-methylpyrrolidin-2-yl) chroman (11)

threo-3-(2,4-Dihydroxyphenyl)-1-(1-methylpyrrolidin-2-yl)propan-1-ol (5.0 g, 19.9 mmol) was reacted with triphenylphosphine (6.0 g, 22.9 mmol) and diethyl azodicarboxylate (4.0 g, 22.9 mmol) in the same manner as described above for erythro-3-(2,4-Dihydroxyphenyl)-1-(1-methylpyrrolidin-2-yl)propan-1-ol. Work-up and chromatographic purification yielded 2.8 g (60%) of 12 as the free base; EIMS (FAB) calcd for $C_{14}H_{19}NO_2$ m/z 233.1416; found, 234.1497 $(M+H)^+$, 100%. The latter was converted to the hydrochloride and recrystallized from absolute ethanol as described above: mp (hydrochloride) 254–256° C.; $^1$H NMR ($CDCl_3$) δ 1.25–2.80 (m, 10H), 2.80–2.90 (s, 3H), 3.20–3.30 (m, 1H), 3.80–4.00 (t, 1H), 6.30–6.90 (m, 3H), 10.0–12.0 (s, 1H). Elemental analysis calculated for $C_{14}H_{19}NO_2 \cdot HCl$: C, 62.43; H. 7.49; N, 5.20. Found: C, 61.44; H, 7.36; N, 5.12.

The intermediate compound threo-3-(2,4-Dihydroxyphenyl)-1-(1-methylpyrrolidin-2-yl)propan-1-ol was prepared as follows.

a. threo-3-(2,4-Dihydroxyphenyl)-1-(1-methylpyrrolidin-2-yl)-propan-1-ol. Compound threo-3-(2,4-Dimethoxyphenyl)-1-(1-methylpyrrolidin-2-yl)propan-1-ol (5.6 g, 20.1 mmol) was reacted with boron tribromide (6.0 mL, 63.9 mmol) under the conditions described above for erythro-3-(2,4-Dimethoxyphenyl)-1-(1-methylpyrrolidin-2-yl)propan-1-ol. After quenching with methanol (10 mL), the mixture was concentrated to a residue. The latter was re-dissolved in absolute ethanol (20 mL) and the solution was added to a solution of sodium (0.55 g, 25.9 mmol) in 30 mL of absolute ethanol. After stirring for 30 minutes, the mixture was filtered to remove precipitated NaBr. Concentration of the filtrate provided a residue which was passed through a short column of silica gel (with ethyl acetate as mobile phase) to yield 5.0 (quant.) of the phenol threo-3-(2,4-Dihydroxyphenyl)-1-(1-methylpyrrolidin-2-yl)-propan-1-ol. $^1$H NMR ($CDCl_3$+DMSO-$d_6$) d 1.20–3.30 (m, 14H), 3.30–3.50 (m, 1H), 4.00–4.6.00 (s, 3H), d 5.90–6.70 (m, 3). EIMS (FAB) calcd for $C_{14}H_{21}NO_3$ m/z 251.1521; found, 252.1603 $(M+H)^+$, 100%.

EXAMPLE 16

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |

-continued

| | |
|---|---|
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound having the formula:

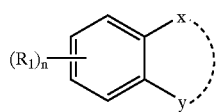

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy, y is $C_2-C_3$ alkyl chain substituted on the carbon adjacent x with $-(CH_2)_mR_e$, and optionally substituted on a carbon other than the carbon bearing $-(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ together with the nitrogen to which they are attached form a 5–6 membered heterocyclic ring; and $R_e$ is a azetidinyl, pyrrolidinyl, 2-piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$alkyl, or $(C_1-C_6)$alkanoyl and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof;

provided $R_1$ is not 6-hydroxy; when y is $-(CH_2)_3-$; n is 1; and $R_e$ is 2-piperidinyl.

2. A compound of claim 1 having the formula:

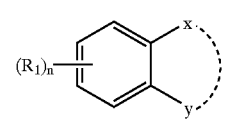

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy;

y is $C_2-C_3$ alkyl chain substituted on the carbon adjacent x with $-(CH_2)_m$Re, and optionally substituted on a carbon other than the carbon bearing $-(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$; m is 0, 1, 2, 3, or 4; n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is a azetidinyl, pyrrolidinyl, 2-piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$ alkyl, or $(C_1-C_6)$alkanoyl;

or a pharmaceutically acceptable salt thereof, provided $R_1$ is not 6-hydroxy; when y is —$(CH_2)_3$—; n is 1; and $R_e$ is 1-methyl-2-piperidinyl.

3. The compound of claim 1 wherein $R_e$ is azetidinyl, pyrrolidinyl, 2-piperidinyl, morpholinyl, or thiomorpholinyl, wherein the ring $R_e$ is substituted on nitrogen with hydrogen, $(C_1-C_6)$alkyl, or $(C_1-C_6)$alkanoyl.

4. The compound of claim 1 having the formula:

[chemical structure with $(R_1)_n$ and $R_e$, X]

or a pharmaceutically acceptable salt thereof.

5. A compound having the formula:

[chemical structure with $(R_1)_n$, X, $R_e$]

wherein $R_1$ is hydrogen, halo, hydroxy, nitro, cyano, trifluoromethyl, trifluoromethoxy, $NR_aR_b$, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, $(C_3-C_6)$ cycloalkyl, or $C(=O)NR_aR_b$;

x is oxy;

n is 1, 2, 3 or 4;

each $R_a$ and $R_b$ is independently hydrogen, $(C_1-C_3$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring;

$R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$ alkyl, or $(C_1-C_6)$alkanoyl, wherein any ring carbon of $R_e$ is optionally substituted with one or more $R_k$; and each $R_k$ is independently halo, hydroxy, nitro, cyano, trifluoromethyl, trifluoromethoxy, $NR_aR_b$, $(C_1-C_6)$ alkyl, $(C_2-C_6)$alkenyl, $(C_2-C_6)$alkynyl, $(C_1-C_6)$ alkoxy, $(C_1-C_6)$alkanoyl, $(C_1-C_6)$alkanoyloxy, $(C_1-C_6)$alkoxycarbonyl, aryl$(C_1-C_6)$alkyl, aryl $(C_2-C_6)$alkenyl, aryl$(C_2-C_6)$alkynyl, aryl$(C_1-C_6)$ alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$ alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$ alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)$ $NR_aR_b$, or a pharmaceutically acceptable salt thereof.

6. A compound having the formula:

[chemical structure with $(R_1)_n$, X, X, $R_e$]

wherein $R_1$ is hydrogen, halo, hydroxy, nitro, cyano, trifluoromethyl, trifluoromethoxy, $NR_aR_b$, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, $(C_3-C_6)$ cycloalkyl, or $C(=O)NR_aR_b$;

x is oxy;

n is 1, 2, 3, or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring;

$R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$ alkyl, or $(C_1-C_6)$alkanoyl, wherein any ring carbon of $R_e$ is optionally substituted with one or more $R_k$; and each $R_k$ is independently halo, hydroxy, nitro, cyano, trifluoromethyl, trifluoromethoxy, $NR_aR_b$, $(C_1-C_6)$ alkyl, $(C_2-C_6)$alkenyl, $(C_2-C_6)$alkynyl, $(C_1-C_6)$ alkoxy, $(C_1-C_6)$alkanoyl, $(C_1-C_6)$alkanoyloxy, $(C_1-C_6)$alkoxycarbonyl, aryl$(C_1-C_6)$alkyl, aryl $(C_2-C_6)$alkenyl, aryl$(C_2-C_6)$alkynyl, aryl$(C_1-C_6)$ alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$ alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$ alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)$ $NR_aR_b$, or a pharmaceutically acceptable salt thereof.

7. The compound of claim 5 wherein $R_e$ is 2-azetidinyl, 1-methyl-2-azetidinyl, 1-methyl-2-pyrrolidinyl, 1-methyl-2-piperidinyl, N-methyl-3-morpholinyl, or N-methyl-3-thiomorpholinyl.

8. The compound of claim 6 wherein $R_e$ is 2-azetidinyl, 1-methyl-2-azetidinyl, 1-methyl-2-pyrrolidinyl, 1-methyl-2-piperidinyl, N-methyl-3-morpholinyl, or N-methyl-3-thiomorpholinyl.

9. The compound erythro-7-Hydroxy-2-(1-methylpyrrolidin-2-yl)chroman; or a pharmaceutically acceptable salt thereof.

10. The compound erythro-7-Hydroxy-2-(1-methylpiperidin-2-yl)chroman; or a pharmaceutically acceptable salt thereof.

11. A compound having the formula:

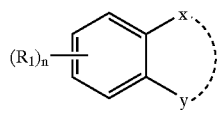

wherein

R$_1$ is hydrogen, halo, hydroxy, nitro, cyano, trifluoromethyl, trifluoromethoxy, NR$_a$R$_b$, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, (C$_3$–C$_6$)cycloalkyl, or C(=O)NR$_a$R$_b$, x is oxy;

y is an optionally unsaturated C$_2$–C$_3$ alkene chain substituted on the carbon adjacent x with —(CH$_2$)$_m$R$_e$, and optionally substituted on a carbon other than the carbon bearing —(CH$_2$)$_m$R$_e$ with halo, hydroxy, nitro, cyano, trifluoromethyl, trifluoromethoxy, NR$_a$R$_b$, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, (C$_3$–C$_6$)cycloalkyl, or C(=O)NR$_a$R$_b$;

m is 0, 1, 2, 3, or 4;

n is 1, 2, 3 or 4;

each R$_a$ and R$_b$ is independently hydrogen, (C$_1$–C$_6$)alkyl, (C$_1$–C$_6$)alkanoyl, aryl, or aryl(C$_1$–C$_6$)alkyl; or R$_a$ and R$_b$ taken together with the nitrogen to which they are attached form a 5–6 membered heterocyclic ring; and R$_e$ is

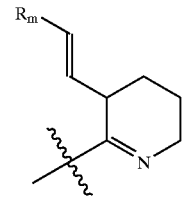

wherein Y is hydrogen or methyl; and R is hydrogen, hydroxy, halogen, (C$_1$–C$_3$)alkyl, (C$_1$–C$_3$)alkoxy, (C$_1$–C$_3$)alkanoyl, cyano, nitro, or amino;

or a pharmaceutically acceptable salt thereof.

12. A compound having the formula:

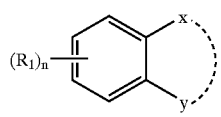

wherein

R$_1$ is hydrogen, halo, hydroxy, nitro, cyano, trifluoromethyl, trifluoromethoxy, NR$_a$R$_b$, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, (C$_3$–C$_6$)cycloalkyl, or C(=O)NR$_a$R$_b$;

x is oxy;

y is an optionally unsaturated C$_2$–C$_3$ alkene chain substituted on the carbon adjacent x with —(CH$_2$)$_m$R$_e$, and optionally substituted on a carbon other than the carbon bearing —(CH$_2$)$_m$R$_e$ with halo, hydroxy, nitro, cyano, trifluoromethyl, trifluoromethoxy, NR$_a$R$_b$, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, or C(=O)NR$_a$R$_b$;

m is 0, 1, 2, 3, or 4;

n is 1, 2, 3 or 4;

each R$_a$ and R$_b$ is independently hydrogen, (C$_1$–C$_6$)alkyl, (C$_1$–C$_6$)alkanoyl, aryl, or aryl(C$_1$–C$_6$)alkyl; or R$_a$ and R$_b$ taken together with the nitrogen to which they are attached form a 5–6 membered heterocyclic ring; and R$_e$ is

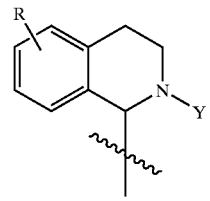

wherein R$_m$ is phenyl or heteroaryl, wherein said phenyl or heteroaryl is optionally substituted with one or more substituents independently selected from halo, hydroxy, nitro, cyano, trifluoromethyl, trifluoromethoxy, amino, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, or (C$_3$–C$_6$)cycloalkyl;

or a pharmaceutically acceptable salt thereof.

13. The compound of claim 1 wherein the stereochemistry at the asymmetric ring carbon bonded to R$_e$ is erythro.

14. The compound of claim 1 wherein the stereochemistry at the asymmetric ring carbon bonded to R$_3$ is threo.

15. The compound of claim 5 or 6 wherein R$_e$ is of the formula:

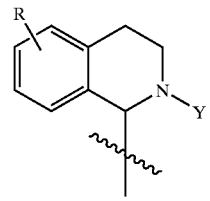

wherein Y is hydrogen or methyl; and R is hydrogen, hydroxy, halogen, (C$_1$–C$_3$)alkyl, (C$_1$–C$_3$)alkoxy, (C$_1$–C$_3$)alkanoyl, cyano, nitro, or amino.

16. The compound of claim 5 or 6 wherein R$_e$ is of the formula:

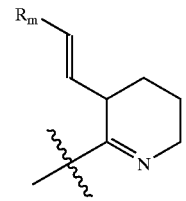

wherein R$_m$ is phenyl or heteroaryl, wherein said phenyl or heteroaryl is optionally substituted with one or more substituents independently selected from halo, hydroxy, nitro, cyano, trifluoromethyl, trifluoromethoxy, amino, (C$_1$–C$_6$)alkyl, (C$_1$–C$_6$)alkoxy, (C$_1$–C$_6$)alkanoyl, (C$_1$–C$_6$)alkanoyloxy, (C$_1$–C$_6$)alkoxycarbonyl, or (C$_3$–C$_6$)cycloalkyl.

17. A compound having the formula:

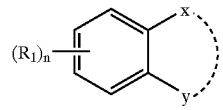

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy;

y is $C_2-C_3$ alkyl chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is

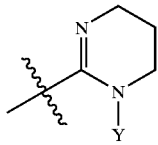

wherein Y is hydrogen or methyl, and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof.

18. A compound having the formula:

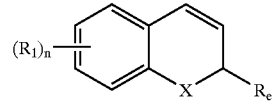

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring;

$R_e$ is

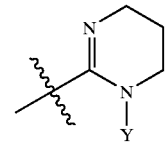

wherein Y is hydrogen or methyl, wherein any ring carbon of $R_e$ is optionally substituted with one or more $R_k$; and each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(c_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof.

19. A compound having the formula:

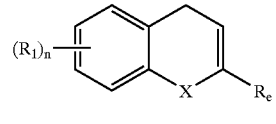

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

x is oxy;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring;

$R_e$ is

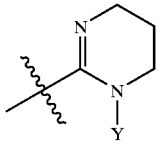

wherein Y is hydrogen or methyl, wherein any ring carbon of $R_e$ is optionally substituted with one or more $R_k$; and each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or C(=O)$NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$, or a pharmaceutically acceptable salt thereof.

20. A compound having the formula:

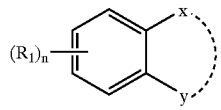

wherein $R_1$ halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$;

x is oxy;

y is $C_2-C_3$ alkyl chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$alkyl, or $(C_1-C_6)$alkanoyl and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or C(=O)$NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$, or a pharmaceutically acceptable salt thereof;

provided $R_1$ is not 6-hydroxy; when y is —$(CH_2)_3$—; n is 1; and $R_3$ is 2-piperidinyl.

21. A compound having the formula:

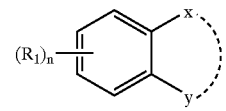

wherein $R_1$ is hydrogen, halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$;

x is oxy;

y is $C_2-C_3$ alkyl chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or C(=O)$NR_aR_b$;

m is 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$alkyl, or $(C_1-C_6)$alkanoyl and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$ alkyl, $(C_2-C_6)$alkenyl, $(C_2-C_6)$alkynyl, $(C_1-C_6)$ alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$, alkynyl, aryl$(C_1-C_6)$ alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$ alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$ alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof;

provided $R_1$ is not 6-hydroxy; when y is —$(CH_2)_3$—; n is 1; and $R_e$ is 2-piperidinyl.

22. The compound threo-7-Hydroxy-2-(1-methylpiperidin-2-yl)chroman; or a pharmaceutically acceptable salt thereof.

23. The compound threo-7-Hydroxy-2-(1-methylpyrrolidin-2-yl)chroman; or a pharmaceutically acceptable salt thereof.

24. A compound having the formula:

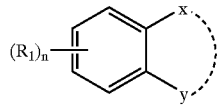

wherein $R_1$ is hydrogen, halo, hydroxy, nitro, cyano, trifluoromethyl, trifluoromethoxy, $NR_aR_b$, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, $(C_3-C_6)$ cycloalkyl, or $C(=O)NR_aR_b$;

x is oxy;

y is $C_2-C_3$ alkyl chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$ alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is 1-methyl-2-azetidinyl, 1-methyl-2-pyrrolidinyl, 1-methyl-2-piperidinyl, N-methyl-3-morpholinyl, or N-methyl-3-thiomorpholinyl;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$ alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof.

25. A compound having the formula:

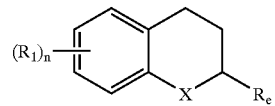

wherein $R_1$ is hydrogen, halo, hydroxy, nitro, cyano, trifluoromethyl, trifluoromethoxy, $NR_aR_b$, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, $(C_3-C_6)$ cycloalkyl, or $C(=O)NR_aR_b$;

x is oxy;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$ alkyl, or $(C_1-C_6)$alkanoyl and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$ alkyl, $(C_2-C_6)$alkenyl, $(C_2-C_6)$alkynyl, $(C_1-C_6)$ alkoxy, $(C_1-C_6)$alkanoyl, $(C_1-C_6)$alkanoyloxy, $(C_1-C_6)$alkoxycarbonyl, aryl$(C_1-C_6)$alkyl, aryl $(C_2-C_6)$alkenyl, aryl$(C_2-C_6)$alkynyl, aryl$(C_1-C_6)$ alkoxy, aryl$(C_1-C_6)$alkanoyl, aryl$(C_1-C_6)$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$ alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$ alkoxy, $(C_1-C_6$alkanoyl, $(C_1-C_6)$alkanoyloxy, $(C_1-C_6)$ alkoxycarbonyl, $(C_3-C_6)$cycloalkyl, or $C(=O)NR_aR_b$, or a pharmaceutically acceptable salt thereof;

provided $R_1$ is not 6-hydroxy; when y is —$(CH_2)_3$—; n is 1; and $R_e$ is 2-piperidinyl.

26. A pharmaceutical composition comprising a compound having the formula:

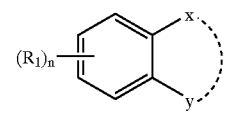

wherein $R_1$ is hydrogen, halo, hydroxy, nitro, cyano, trifluoromethyl, trifluoromethoxy, $NR_aR_b$, $(C_1-C_6)$ alkyl, $(C_1-C_6)$alkoxy, $(C_1-C_6)$alkanoyl, $(C_1-C_6)$ alkanoyloxy, $(C_1-C_6)$alkoxycarbonyl, $(C_3-C_6)$ cycloalkyl, or $C(=O)NR_aR_b$;

x is oxy;

y is $C_2-C_3$ alkyl chain substituted on the carbon adjacent x with —$(CH_2)_mR_e$, and optionally substituted on a carbon other than the carbon bearing —$(CH_2)_mR_e$ with halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$;

m is 0, 1, 2, 3, or 4;

n is 1, 2, 3 or 4;

each $R_a$ and $R_b$ is independently hydrogen, $(C_1-C_6)$alkyl, $(C_1-C_6)$alkanoyl, aryl, or aryl$(C_1-C_6)$alkyl; or $R_a$ and $R_b$ taken together with the nitrogen to which they are attached form a 5–6 membered heterocyclic ring; and $R_e$ is a azetidinyl, pyrrolidinyl, piperidinyl, morpholinyl, 1,2,3,4-tetrahydroisoquinolyl, 3,4,5,6-tetrahydropyridyl, or thiomorpholinyl wherein the ring $R_e$ is substituted on nitrogen with hydrogen, $(C_1-C_6)$alkyl, or $(C_1-C_6)$alkanoyl and wherein any ring carbon of $R_e$ is optionally substituted with one or more $R_k$;

each $R_k$ is independently halo, hydroxy, nitro, cyano, trifluoromethyl, trifluoromethoxy, $NR_aR_b$, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, aryl$(C_1-C_6)$alkyl, aryl$(C_2-C_6)$alkenyl, aryl$(C_2-C_6)$alkynyl, aryl$(C_1-C_6)$alkoxy, aryl$(C_1-C_6)$alkanoyl, aryl$(C_1-C_6$alkanoyloxy, aryl$(C_1-C_6)$alkoxycarbonyl, heteroaryl$(C_1-C_6)$alkyl, heteroaryl$(C_2-C_6)$alkenyl, heteroaryl$(C_2-C_6)$alkynyl, heteroaryl$(C_1-C_6)$alkoxy, heteroaryl$(C_1-C_6)$alkanoyl, heteroaryl$(C_1-C_6)$alkanoyloxy, heteroaryl$(C_1-C_6)$alkoxycarbonyl, $(C_3-C_6)$cycloalkyl, or $C(=O)NR_aR_b$;

wherein each aryl or heteroaryl is optionally substituted with one or more substituents independently selected from halo, hydroxy, nitro, cyano, trifluoromethyl, trifluoromethoxy, $NR_aR_b$, $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, $(C_3-C_6)$cycloalkyl, or $C(=O)NR_aR_b$, or a pharmaceutically acceptable salt thereof;

provided $R_1$ is not 6-hydroxy; when y is —$(CH_2)_3$—; n is 1; and $R_e$ is 2-piperidinyl a pharmaceutically acceptable carrier.

27. A pharmaceutical composition comprising a compound as described in any of claims 2, 5, 6, 9, 10, 11, 12, 17, 18, 19, 20, 21, 22, 23, 24, and 25 and a pharmaceutically acceptable carrier.

28. A method for activating a nicotine receptor in mammalian tissue comprising contacting the tissue with an effective nicotine receptor activating amount of a compound of claim 1, 2, 5, 6, 9, 10, 11, 12, 17, 18, 19, 20, 21, 22, 23, 24, or 25.

29. A method for activating a nicotine receptor in mammalian tissue comprising contacting the tissue in vitro with an effective nicotine receptor activating amount of a compound of claim 1, 2, 5, 6, 9, 10, 11, 12, 17, 18, 19, 20, 21, 22, 23, 24, or 25.

30. A method for activating a nicotine receptor in a mammal comprising administering an effective nicotine receptor activating amount of a compound of claim 1, 2, 5, 6, 9, 10, 11, 12, 17, 18, 19, 20, 21, 22, 23, 24, or 25 to the mammal.

* * * * *

UNITED STATES PATENT AND TRADEMARK OFFICE
CERTIFICATE OF CORRECTION

PATENT NO.    : 6,846,817 B2
DATED         : January 25, 2005
INVENTOR(S)   : S. Mbua N. Efange It is certified that error appears in the above-identified patent and that said Letters Patent is hereby corrected as shown below:

<u>Title page, Item [54] and Column 1, line 1,</u>
Title, insert -- BENZOFURAN AND CHROMAN -- before "NICOTINE".

<u>Column 32,</u>
Line 1, after "oxy" delete "," insert -- ; --.
Line 15, after "$R_b$" insert -- taken --.
Line 61, after "Re" and insert -- $R_e$ --.

<u>Column 33,</u>
Line 38, after "Rb" delete "," and insert -- ; --.
Line 42, delete "$(C_1-C_3)$alkyl" and insert -- $(C_1-C_6)$alkyl --.

<u>Coumn 34,</u>
Lines 6-10, delete " 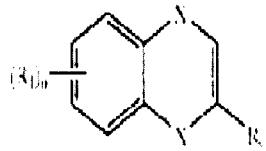 " and insert -- 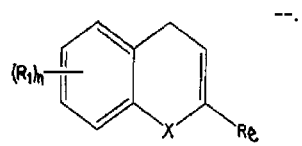 --.

Line 21, after "3" delete ",".

<u>Column 35,</u>
Line 14, after "$R_b$" delete "," and insert -- ; --.

<u>Column 36,</u>
Line 32, delete "$R_3$" and insert -- $R_e$ --.

UNITED STATES PATENT AND TRADEMARK OFFICE
CERTIFICATE OF CORRECTION

PATENT NO. : 6,846,817 B2
DATED : January 25, 2005
INVENTOR(S) : Efange

It is certified that error appears in the above-identified patent and that said Letters Patent is hereby corrected as shown below:

Column 37,
Line 62, delete "$_{(c1}$" and insert -- $(C_1$ --.

Column 38,
Lines 39 and 48, delete "$_{(c1}$" and insert -- $(C_1$ --.

Column 39,
Line 64, after "$R_b$" delete "$_{is}$" and insert -- is --.

Column 40,
Line 29, delete "$R_3$" and insert -- $R_e$ --.

Column 42,
Line 44, delete "$(C_1$-$C_6$alkanoyl" and insert -- $(C_1$-$C_6)$alkanoyl --.

Column 43,
Line 25, delete "$(C_1$-$C_6$alkanoyloxy" and insert -- $(C_1$-$C_6)$alkanoyloxy --.

Signed and Sealed this

Eighth Day of November, 2005

JON W. DUDAS
*Director of the United States Patent and Trademark Office*